United States Patent
Bazito et al.

(10) Patent No.: US 9,655,832 B2
(45) Date of Patent: May 23, 2017

(54) COSMETIC COMPOSITION FOR RESTORING LIPIDIC LAYER OF THE STRATUM CORNEUM IN ORTHORHOMBIC

(75) Inventors: Alexandra Bazito, São Paulo (BR); Maria Regina Bartuccio Raponi, São Paulo (BR); Nelson Luis Perassinoto, Campinas (BR); Liliana Calore Brenner, São Paulo (BR)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 13/698,870

(22) PCT Filed: May 24, 2011

(86) PCT No.: PCT/BR2011/000164
§ 371 (c)(1),
(2), (4) Date: Jan. 24, 2013

(87) PCT Pub. No.: WO2011/147011
PCT Pub. Date: Dec. 1, 2011

(65) Prior Publication Data
US 2013/0116194 A1    May 9, 2013

(30) Foreign Application Priority Data
May 25, 2010  (BR) ..................................... 1003486

(51) Int. Cl.
| A61K 8/60 | (2006.01) |
| A61K 8/64 | (2006.01) |
| A61Q 19/00 | (2006.01) |
| A61K 8/34 | (2006.01) |
| A61K 8/44 | (2006.01) |

(52) U.S. Cl.
CPC ............... *A61K 8/64* (2013.01); *A61K 8/342* (2013.01); *A61K 8/345* (2013.01); *A61K 8/44* (2013.01); *A61K 8/60* (2013.01); *A61Q 19/00* (2013.01); *A61Q 19/007* (2013.01)

(58) Field of Classification Search
CPC .......... A61K 8/342; A61K 8/345; A61K 8/44; A61K 8/64; A61K 8/60; A61Q 19/007; A61Q 19/00
See application file for complete search history.

(56) References Cited

U.S. PATENT DOCUMENTS

| 5,908,697 A * | 6/1999 | Roux et al. ................ 428/402.2 |
| 5,932,234 A | 8/1999 | Simonnet et al. |
| 6,342,238 B1 | 1/2002 | Simonnet et al. |
| 2009/0041691 A1 * | 2/2009 | Candau et al. ................ 424/60 |
| 2009/0142381 A1 | 6/2009 | Agarelli et al. |

OTHER PUBLICATIONS

Definition of derivative, from http://cancerweb.ncl.ac.uk/cgi-bin/omd?query=derivative, pp. 1-5, accessed Jul. 7, 2005.*
Som et al, Status of surfactants as penetration enhancers in transdermal drug delivery, J Pharm Bioall Sci, 2012, 4, pp. 2-9.*

* cited by examiner

*Primary Examiner* — Julie Ha
*Assistant Examiner* — Li Ni Komatsu
(74) *Attorney, Agent, or Firm* — Thompson Hine LLP; William J. Davis

(57) ABSTRACT

The present invention refers to a cosmetic composition of the oil-in-glycol type comprising (a) at least one sucrose non-ionic surfactant or derivatives thereof, (b) at least one fatty alcohol, (c) at least one glycol and (d) at least one ingredient selected from aminoacid and/or peptide, as well as associated uses, products and methods. The composition of the invention is capable of restoring the cutaneous barrier, reorganizing the lipidic layer of the stratum corneum in orthorhombic, conceding hydration, renewal and cellular energization in the long run. In a particular embodiment, said composition can be used simultaneously as an emulsifying system for preparing cosmetic products, for example, in the preparation of creams, lotions, etc.

9 Claims, 34 Drawing Sheets

COSMETIC COMPOSITION FOR RESTORING LIPIDIC LAYER OF THE STRATUM CORNEUM IN ORTHORHOMBIC

CROSS-REFERENCE TO RELATED APPLICATIONS

This application is a 371 of PCT/BR2011/000164 filed on May 24, 2011 and claims foreign priority to Brazilian patent Application No. PI1003486-2 filed on May 25, 2010, the specifications of which are hereby incorporated in their entireties.

FIELD OF THE INVENTION

The present invention refers to a cosmetic composition of the oil-in-glycol type comprising (a) at least one sucrose non-ionic surfactant or derivatives thereof, (b) at least one fatty alcohol, (c) at least one glycol and (d) at least one ingredient selected from aminoacid and/or peptide. The composition of the invention restores the cutaneous barrier, reorganizing the lipidic layer of the stratum corneum in orthorhombic and, simultaneously, acts as an emulsifying system for preparing cosmetic products.

BACKGROUND OF THE INVENTION

The skin is an organ from to the tegumentary system (along with hair and hairs, nails, sweat and sabeceous glands) and the main functions of which are to protect the subjacent tissues, regulate the somatic temperature, maintain water homeostasis, nutrient reserve and also contain sensitive nerve terminations.

This organ has three layers or strata: epidermis (most superficial), dermis (intermediary) and subcutaneous hypodermis (technically external to the skin, but functionally related). There are also various organs attached, such as hair follicles, sweat and sebaceous glands.

The epidermis is a stratified epithelium, that is, a tissue formed by juxtaposed cells, which is separated from the dermis by a basal membrane. It comprises five layers or strata: germinative, spinous, granular, lucid and corneum. The purpose of its constitution and structure is to keep the balance of the surface of the body, preventing physical damage (e.g. rigors of temperature, humidity and drying, traumas, ultraviolet radiation), chemicals (e.g. alkalis, acid soaps) and biological (e.g. microorganisms, such as virus, fungi and bacteria).

Most of the cells of the epidermis are comprised of keratinocytes. In constant renewal, keratinocytes become corneocytes. In this natural process, each keratinocyte which is produced in the basal layer migrates to the surface, also producing on this trajectory lipids and proteins, of which the most important is keratin. As soon as it becomes full of keratin, the keratinocyte loses its nucleus, also changing its physical form (from cubic to hexagonal and flattened), becoming a corneocyte, which becomes evermore peripherical, and ending up flaking and falling off. The corneocytes constitute the outermost layer of the epidermis, called corneum layer or stratum corneum.

Over recent decades, many studies have been carried out with the objective of elucidating the structure, workings and role of the stratum corneum.

The 'brick and mortar' structural model proposes that the stratum corneum is a structure in which the cells of the corneocytes are arranged in successive layers, and the link between them is realized by the intercellular 'mortar', which comprises a lipidic matrix organized in bilayers. It may include ceramides, cholesterol and certain fatty acids which have relatively large hydrocarbon chains and unsaturations.

The lipids of the stratum corneum are contained in cytoplasmic organelles, called lamellar bodies, which can be found in the upper layer of the spinous stratum. The lamellar bodies are formed in the endoplasmic reticulum and, by way of exocytosis; its content is expelled in the intercellular space, in the transition from granular stratum to stratum corneum.

The corneocytes jointly with the lipids produced in the epidermis and sebaceous glands (epidermic and sebaceous, respectively), in addition to the water with mineral salts originating from sudoresis (electrolytes), form the cutaneous barrier, fundamental to the integrity of the protective function of the skin, as it keeps the pH ideal, controls the diffusion of molecules or gases such as oxygen and carbon dioxide and homeostasis of the water levels.

The intercellular lamellar lipids are organized in three phases: crystalline, hexagonal and orthorhombic. The predominant phase is the orthorhombic. This organization provides an effective barrier for the passage of water and any disturbance in this organization results in undesirable drying conditions (dry or unhydrated skin).

Hydrated skin, in turn, is highly desirable because it is perceived as soft-to-the-touch skin, having malleability, without opacity or flaking.

It is recognized that not all emollients are the same in terms of their capacities to humidify the human stratum corneum (hydrate the skin). Skin humidifiers can be classified as moisturizers or occlusion agents, according to its action mechanism.

Moisturizers are small, hygroscopic molecules that penetrate into the stratum corneum and subsequently act as moisturizers. In order that moisturizers may act by this mechanism, they must be not only hygroscopic, but must penetrate the skin. Glycerin is the most well-known moisturizing ingredient. It is extremely hygroscopic and attracts water molecules. Besides this one, glycols and other polyhydroxy molecules, such as propylene glycol, butylene glycol, glucose, sucrose and sorbitol also act by this mechanism.

The second group, occlusion agents, generally involves lipophilic materials which contain long, unbranched alkyl chains, without double bonds. It is an essential requirement that these agents be substantive with the skin and capable of aligning their hydrocarbon tails, to create an occlusive layer on the surface of the skin. This layer prevents water evaporation from the skin and, therefore, the water content of the stratum corneum is increased. The moisturizers that act by this mechanism are generally hydrocarbons, such as mineral oil and petrolatum.

Besides using ingredients having a moisturizing nature, certain complex cosmetic compositions have been developed with the purpose of providing the perception of hydrated skin. Many of them use specific active principles, sometimes of a high commercial value, as well as formulation strategies that require the use of a large number of raw materials and strict quality control.

In terms of structuring, the most common formulations are of the oil-in-water type, for example, such as described in patent documents WO05108383 and U.S. Pat. No. 5,925,364. There are also formulations of the oil-in-glycerin type, for example, such as those described in patent documents WO0056346, U.S. Pat. No. 6,342,238, WO06119042 and WO0224152. The latter, designed for the transport or permeation of active compounds by way of layers of the skin or merely its protection against degradation, does not remedy the drawbacks of skin drying either immediately and/or in the long run.

As well recognized in the state of the art, cosmetic compositions are generally prepared with the use of anionic, cationic, amphoteric and/or non-ionic surfactants. These compounds are described, for example, in the work entitled *Sufactants*, by Martin Rieger, published by *Society of Cosmetic Chemists* in 1997 (incorporated as a reference herein).

Esters derived from carbohydrate constitute a subclass of non-ionic surfactants. These surfactants do not have a load at the pH levels normally used in the cosmetics sector. Owing to their characteristics, they are used in isolation or in combination, in different formulation strategies, for example, as described in documents WO05108383, U.S. Pat. No. 5,925,364, JP10231229, US 20070286835 and WO0929046. In general, the technique teaches their use in low concentrations, between 0.2-2.5% in relation to the total weight of the composition.

Further, in relation to degradation, it is important to consider that most compositions of the oil-in-glycerin type, containing non-ionic surfactants or not, use ingredients that present unsaturations, that is they are more susceptible to oxidation and, therefore, less stable, for example, vegetable oils, ceramides, cholesterol, etc. In general, these compositions seek identity with the composition of the skin which, for example, contains ceramides as one of its main components.

Wiechers et al. (*Skin Moisturization*, second edition, Informa healthcare, USA, 2009), introduced a third action mechanism associated to skin moisturization, that of breakdown of the lipidic barrier.

The experiments revealed that different distributions of water in the stratum corneum, as a consequence of applying two emollients, could have been caused by different interactions with the organization of the skin lipids.

Applying moisturizers to the skin not only attracts and maintains water, but interferes in the configuration of the lipidic phases.

It was concluded that the dysfunction in the workings of the barrier of the stratum corneum is at the heart of many problems associated to skin with altered balance. Therefore, normalizing the structure of the lamellar lipids would therefore be a strategy to be pursued.

Thus, the correct water gradient can only be maintained in the long run if the skin barrier is completely functional. Therefore, if the lipidic phase is stabilized in orthorhombic, then the skin barrier is appropriately restored and all the symptoms of skin with altered balance will be reversed, such that the vicious cycle of imbalance can be broken. Although molecules such as glycerin and mineral oil may temporarily solve the drawbacks of dry skin, they knowingly do not act on the causal problem, such as modulating the behavior of the lipidic phase, restoring its orthorhombic organization.

Even though this new mechanism has been established, there are no products efficient at stabilizing the lipidic phase, restoring the orthorhombic structuring thereto.

Stabilizing the lipidic phase in orthorhombic leads to an increase in water retention of the stratum corneum by natural means; that is the skin barrier will be responsible for the necessary moisturizing response, by means of efficient control of the water flow. This leads to a more efficient and long-lasting response to the problem of dry skin, as well as sensorially more pleasurable than that which the use of traditional moisturizing agents may offer only as a temporary means, due to its adverse effects in disorganizing the lipidic layer.

So the need remains for cosmetic compositions that act directly in reorganizing the lipidic layer in orthorhombic and, consequently, providing a prolonged effect, also avoiding the use of ingredients susceptible to oxidation and the direct action in deeper layers of the skin (permeation).

BRIEF DESCRIPTION OF THE DRAWINGS

The present invention is illustrated by means of the following drawings.

DESCRIPTION OF THE INVENTION

Figure 1A:
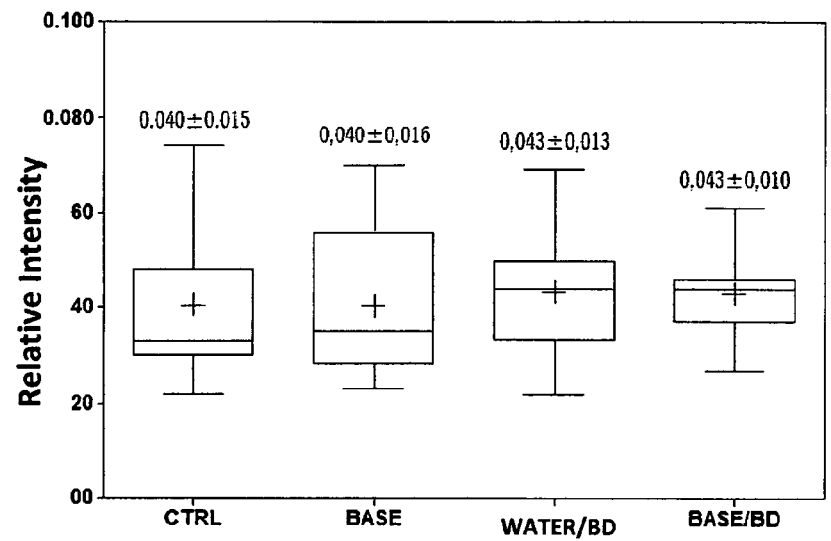
FIG. 1A shows average basal values obtained for each study group, for the parameter Ort.

In the search to act directly in reorganizing the lipidic layer, a cosmetic composition was developed that acts on the outermost part of the epidermis, the stratum corneum, developing its good behavior, by means of structural reorganization of the intercellular lipids in orthorhombic.

Surprisingly, by using a specific combination of components known in the art and that knowingly act differently to that sought, there is proposed a cosmetic composition that acts in an immediate manner in terms of hydration, providing pleasant sensations, and also solving the causal problem of dry skin, acting in a prolonged manner and avoiding the side effects known in the art.

Differently to the prior art, the composition according to the present invention avoids the use of compounds that when used freely in the composition, may be susceptible to degradation, for example, vegetable oils, ceramides, cholesterol, among others. Therefore, there is proposed an alternative to those compositions of the prior art, which merely seek to present identity to the compounds naturally present in skin layers.

Therefore, the object of the present invention is a cosmetic composition of the oil-in-glycol type comprising (a) at least one sucrose non-ionic surfactant or derivatives thereof, (b) at least one fatty alcohol, (c) at least one glycol and (d) at least one ingredient selected from aminoacid and/or peptide.

The non-ionic surfactant of the sucrose type is preferably an ester, and may be one or more from among sucrose stearate, sucrose tristearate, sucrose hexaerucate and sucrose tribehenate. Particularly, it is one or more from among sucrose stearate and sucrose tristearate, in an amount of at least 10% by weight, more particularly between 10 and 20% by weight.

When not indicated otherwise, the percentages by weight indicated for a certain ingredient are related to the total weight of the final cosmetic composition.

More particularly, the composition according to the present invention contains as surfactant a mixture of sucrose stearate and sucrose tristearate, in the ratio of 2:1.

The fatty alcohol is particularly selected from among those having a carbon chain of $C_{10}$ to $C_{22}$, preferably behenyl and isocetyl alcohols, particularly in mixture, in an amount that may vary from 10 to 20% by weight.

The term glycol, in the sense used herein, must be understood broadly, including glycol compounds having at least two hydroxyls, such as butylene glycol or propylene glycol or preferably having at least three hydroxyls, such as 1,2,3-propantriol. The amount of glycol varies particularly between 40 and 65% by weight, more particularly between 50 and 60% by weight.

The preferred aminoacid according to the present invention is selected from among arginin, its salts, esters and others derivatives. In a particular embodiment, an ester of arginin may be used as stearate or, also, a fatty acid may be included in the composition with the purpose of esterifying arginin. The esterification of arginin leads to greater absorption, as well as an improvement in the function of this aminoacid. The preferred fatty acid for this particular embodiment is stearic acid, which will form arginin stearate inside the cosmetic composition itself. The amount of fatty acid must be adjusted to be sufficient to esterify the amount of aminoacid used in the composition according to the present invention. This is because the presence of a free fatty acid is not responsible for the effects of the composition, as the presence of a free fatty acid may generate undesirable results.

The peptide may be the tripeptide-3 (a synthetic peptide containing glycine, serine and valine), which can be used in the form of a pre-mixture with water and glycol butylene, such as that commercialized as Atpeptide, by the company ISP—International Specialty Products.

In a particular embodiment, a cosmetic composition contains 5 to 30% by weight of the ingredient (d), being particularly preferable a mixture of about 2% of arginin and about 5% of Atpeptide.

The cosmetic composition according to the invention can be used both directly on the skin as an additive in the preparation of cosmetic products. In this case, the composition according to the invention acts both (a) as cosmetic active ingredient restorative of the organization of the lipidic phase to promote hydration, improves cellular renewal and energization (calcium gradient) and (b) as the emulsifying system itself. And even used as an emulsifier, the composition according to the invention does not significantly decrease its restorative action.

Therefore, other objects of the present invention are the use of the cosmetic composition as an additive that provides, simultaneously, the active effects discussed previously and acts as an emulsifying system, in the preparation of cosmetic products, as well as the cosmetic products themselves containing said composition. These are prepared with cosmetically compatible excipients to obtain a cosmetic product, such as creams, balms, pastes, emulsions, gels, soap in bar or liquid form, sera, combined cosmetic forms or others known in the art.

The amount of composition according to the present invention to be used as additive in cosmetic products may vary from 1 to 30% by weight, being particularly preferable about 5% by weight.

The preparation of the composition according to the invention takes into account two criteria: come as close as possible to the vitreous transition point of the lipoprotein barrier and come close to the configuration thereof in terms of crystal structure.

In this sense, the cosmetic composition according to the present invention is in the form of oil-in-glycol, which enables a reduction in the vitreous transition temperature, being closer to that of the barrier, in comparison with more traditional cosmetic compositions, for example, oil-in-water or water-in-oil.

This characteristic surprisingly allows both the rearrangement in the gradient of the loss of transepidermic water in various layers of the epidermis, which results in an increase of hydration by means of repairing the lipoprotein barrier, and a rearrangement in the calcium gradient, especially in the interface with the junction of the corneus layer. This result allows us to suppose, without being linked to theory, that there is a simultaneous increase of cellular renewal and, consequently, an increase in cellular energy.

Additionally, the use of compounds with branched fatty chains having a number of carbons similar to that of the lipoprotein barrier, also assists in reducing the vitreous transition point of the composition, which is an unexpected effect.

As a result, as of the approximation between the points of vitreous transition of the cosmetic composition of the present invention and of the substrate, biosensor action was noted, that is it enables an interaction with the barrier, without aggressions, but rather with restoration of the structural organization in orthorhombic.

Therefore, the main biochemical interactions and energy processes of the skin were allowed to process in a harmonious manner, which does not occur with traditional moisturizers, because besides increasing the vitreous transition point of the system, they cause occlusion and breakdown in the long run. Furthermore, traditional moisturizers may hydrate immediately, yet owing to the differences in polarity with the barrier and the vitreous transition point, promoting a breakdown of the fatty organization and consequently allowing the loss of cellular energy, whereby reducing the speed of cellular renewal.

The same happens with systems that facilitate the permeation so as to destructure the original organization of the barrier and those that are well below the vitreous transition point thereof. These also contribute to increase the water loss gradient, dehydrating the skin. In the first moment they even assist the cellular renewal, but after the constant breakdown of the barrier, the process is reversed.

These drawbacks are avoided with the use of the cosmetic composition according to the present invention, because it reorganizes the barrier, promoting a long-term effect, that is even interrupting the use and does not leave the skin with an oily appearance.

Therefore, other objects of the present invention are the use of the cosmetic composition in restoring the lipid barrier in orthorhombic and a method for restoring the lipidic barrier in orthorhombic which consists of applying the composition of the invention on the skin in need, directly or carried in a cosmetic product.

The examples below are to illustrate aspects of the present invention, but are not limitative in character.

EXAMPLES

Example 1

Composition According to the Present Invention

The table below shows a variant of the composition according to the present invention. Said composition was prepared based on the mixture of the ingredients in the amounts indicated, maintaining the addition of phases described in the table.

TABLE 1

| Ingredient | Commercial Name | % by weight |
|---|---|---|
| Phase A | | |
| Sucrose stearate | Surfhope 1816 | 10 |
| Sucrose tristearate | Surfhope 1803 | 5 |
| Isocetyl alcohol | Ceraphyl ICA | 8 |
| Behenic alcohol | Lanette 22 | 11 |
| Stearic acid (*) | Stearic Acid | 4 (*) |
| Phase B | | |
| Glycerin | Glycerin | 20 |
| Arginine | L-Arginine | 2 |
| Phase C | | |
| Glycerin | Glycerin | 35 |
| Water/Butylene Glycol/Tripeptide-3 | Atpeptide | 5 |

(*) The amount of stearic acid is sufficient for esterifying the arginine ingredient, forming arginine stearate.

Example 2

Preparing Cosmetic Products Containing the Composition of Example 1

The table below shows two different cosmetic products, solution and cream, containing a variant of the composition according to example 1.

| Ingredient | SAMPLE A Base Cream | SAMPLE B Solution with composition of Example 1 | SAMPLE C Base Cream with composition of Example 1 |
|---|---|---|---|
| Water | 85.19 | 93.84 | 80.19 |
| Optiphen | 1.00 | 1.00 | 1.00 |
| Composition of Example 1 | 0.00 | 5.00 | 5.00 |
| Edta | 0.05 | 0.00 | 0.05 |
| Glyceryl monostearate | 2.50 | 0.00 | 2.50 |
| Cetostearyl Alcohol | 2.50 | 0.00 | 2.50 |
| Dimethicone 200-350 | 1.00 | 0.00 | 1.00 |
| Mineral Oil | 2.00 | 0.00 | 2.00 |
| Triethanolamine (*) | 0.60 | 0.00 | 0.60 |
| Stearate acid (*) | 3 | 0 | 3 |
| Xanthan Gum | 0.16 | 0.16 | 0.16 |
| Glycerin | 2.00 | 0.00 | 2.00 |

(*) included in sufficient amount to form an interphasic emulsifying agent, triethanolmine stearate, by an acid-based reaction occurring in situ between the stearic acid and the triethanolamine, no free stearic acid remaining in the composition.

Example 3

Efficiency Test

With the purpose of performing an in vivo evaluation of the organizational behavior of the lipid barrier of the stratum corneum, in light of the action of different cosmetic products with and without the inclusion of a composition according to the present invention, the FTIR-ATR (Fourier Transform Infrared Spectroscopy using Attenuated Total Reflectance) technique associated to x-ray diffraction was used. This technique has been applied to evaluate the organization of the lipids in the lamellar layers of the stratum corneum, using in vitro systems.

Samples

Samples prepared in accordance with table 1 of example 2 were used:
Sample A—comparative Base Cream.
Sample B—Aqueous solution with 5% of a composition according to the present invention.
Sample C—Base Cream with 5% of a composition according to the present invention.

Selecting the Volunteers

Sixty (60) women were selected in accordance with the following inclusion criteria: aged between 32 and 53 years, of feminine sex, phototype between II and VI (Fitzpatrick classification) and dry and intact skin in the study region.
Additionally, the volunteers had no characteristics or used substances that might compromise the results of the study.

Preparing the Panel

The participating volunteers were instructed to suspend the use of any product of topical use on the arms 48 hours before the start of the study.
On the day of the study, the volunteers were pre-acclimatized for 20 minutes in the study environment, controlled at ±2° C. and 55±5% of relative air humidity.

Study Groups

The volunteers were randomly divided into 4 study groups each having 15 participants, 1 being designated as control, without applying any cosmetic products during the course of the study period.

| | Identification | Applied Product |
|---|---|---|
| 1 | Control | None |
| 2 | Base | Sample A |
| 3 | Water/BD (*) | Sample B |
| 4 | Base/BD (*) | Sample C |

(*) "BD" refers to an internal code for referencing the composition according to the present invention.

Study Procedure

The study was carried out considering three days of readings: D1, D14 and D21.
On the first day (D1) the basal spectrum of the skin, t0, was obtained and thereafter the product was applied, according to the study group. Sequentially, new spectra were obtained 2, 4, 6 and 24 hours after the single application of the product (kinetics). The volunteers were then instructed to use the products for 14 days.

After 14 days of using the product (D14), a fresh basal spectrum of the skin was obtained 24 h after the latest application of the product. In sequence, the product was again applied and new spectra of the skin were obtained 2, 4, 6 and 24 hours after the single application. The products in use were collected and the volunteers were instructed not to apply any cosmetic on their forearms for a further 7 days.

Seven (7) days after the latest application of the product (D21, washout period) a fresh basal spectrum of the skin was obtained.

Equipment

The spectra were obtained using the equipment FTIR Equinox 55—Bruker, with a cell from ATR PIKE Technologies 6571 with ZnSe crystal, using the Software Opus NT—Version 3.

The skin spectra were obtained by positioning the marked site on the skin of the volar forearm of the volunteer (site) on the ATR (Attenuated total reflectance) cell.

Readings were obtained in the region of 400 to 4000 cm$^{-1}$ of the average infrared, in an FTIR (Fourrier Transform Infrared) configuration, with accumulation of 20 scans and spectral resolution of 2 cm$^{-1}$. application Sites On a volar forearm of each volunteer, an area called site was marked, measuring 2.5×4.0 cm, in the average position between the wrist and the elbow. Applying the sample On days D1 and D14, 20.0μL of the product was applied on the site with the assistance of a micropipette, massaging it over the area of the site until full absorption, using a disposable finger cuff.

Climactic Conditions

Before beginning the readings, the volunteers were acclimatized for 20 minutes in an environment kept at 22±2° C. and 55±5% of relative air humidity.

Analyzing and Interpreting the Data Softwares

Equipment control software: OPUS NT®—Version 3 (Bruker, EUA, 2005).

Analysis of spectra: Origin Pro 8 SRO (Origin Lab Corp, USA, 2007).

Statistical Analysis: GRAPHAD™ PRISM® 4.03 (Graph Pad Software Inc, USA, 2007).

Analysis and Interpretation

Based on the gross spectra, a calculation was made of the second order derivatives with smoothing of 5 points of the FFT (Fast Fourier Transform) type. The areas relating to the absorption bands of 1453, 1465 and 1537 cm$^{-1}$ were then obtained.

The value of the area obtained for absorption in 1537 cm$^{-1}$ refers to amida II and was used as an internal reference for normalization of the areas of the absorptions of interest, at 1453 and 1465 cm$^{-1}$.

In the hexagonal packing, the methylene groups of the lipidic chains are symmetrically apart, such that the symmetric angular deformation on the plane ($\delta_s CH_2$) generates a single absorption band of approximately 1465 cm$^{-1}$.

In the case of the orthorhombic packing, the asymmetry in the side distancing of the lipidic chains generates a coupling in the band ($\delta_s CH_2$), resulting in a doublet, with absorptions at 1453 cm$^{-1}$ and 1465 cm$^{-1}$.

Since in the crystalline lamellar structure in the stratum corneum there is a coexistence of the hexagonal and orthorhombic packing of the lipids, two absorption bands are noted in the spectrum. The orthorhombic structure is singularly responsible for the absorption at 1453 cm$^{-1}$, which appears like a shoulder on the band in 1465 cm$^{-1}$, more intense due to being constituted by the absorptions of the very orthorhombic and hexagonal structure (doublet).

Therefore, the absorption intensity at 1453 cm$^{-1}$ can be used to accompany the fraction of the orthorhombic phase in the crystalline structure, Ort. The greater the absorption, the greater the fraction of this type of packing in the crystalline structure (Ort=$I_{1453}/I_{1537}$).

Considering the symmetry in the doublet packing of the orthorhombic type, the difference in intensity between the bands in 1465 cm$^{-1}$ (Hex+Ort) and 1453 cm$^{-1}$ (Ort) can be used to evaluate the hexagonal packing individually, Hex (Hex=$I_{1465}/I_{1537}-I_{1453}/I_{1537}$).

The total crystallinity of the lamellar structure, CT, may be accompanied based on the intensity of the absorption of the hexagonal and orthorhombic structures, as the increase of the liquid lamellar phase causes an enlargement of the bands and a reduction of the absorption intensities (CT=Hex +Ort).

The results of the study comprise two information blocks. The first block refers to the modification in the crystallinity of the lamellar layers of the corneum extract, promoted by the treatment and always evaluated 24 hours after the latest application of the product to the skin, when applicable. These results refer to the effectiveness of the longest duration of the treatment.

The second block evaluates the immediate effect promoted by the product in a time interval of up to 24 hours after application, whose kinetics (2, 6 and 24 hours) was evaluated on the first day of the study (first contact of the skin with the product) and again after 14 days of continued use of the product.

This procedure is designed to obtain information on how the continued use of the product interferes with the immediate effectiveness after applying the product to the skin.

Evaluating the Initial Homogeneity of the Study Groups

Figure 1B:
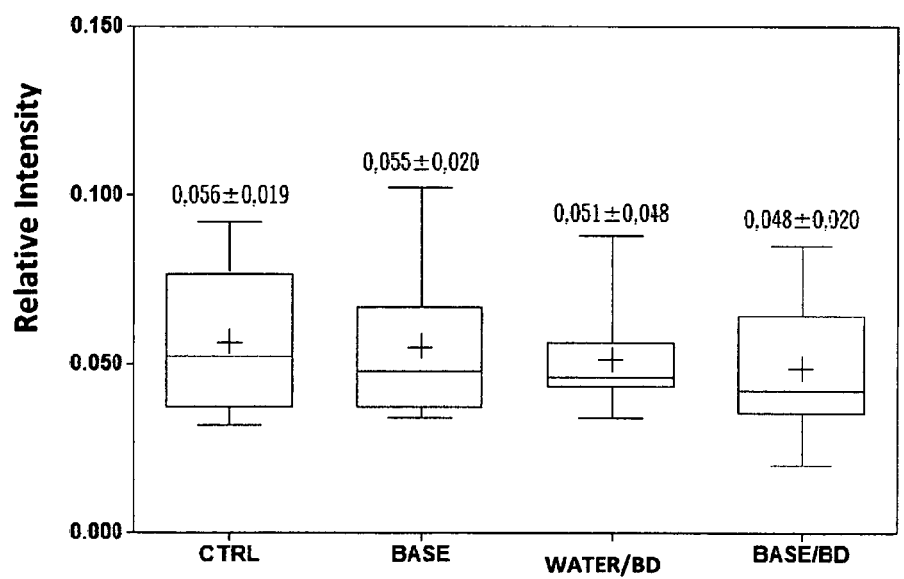
FIG. 1B shows average basal values obtained for each study group, for the parameter Hex.
Figure 1C:
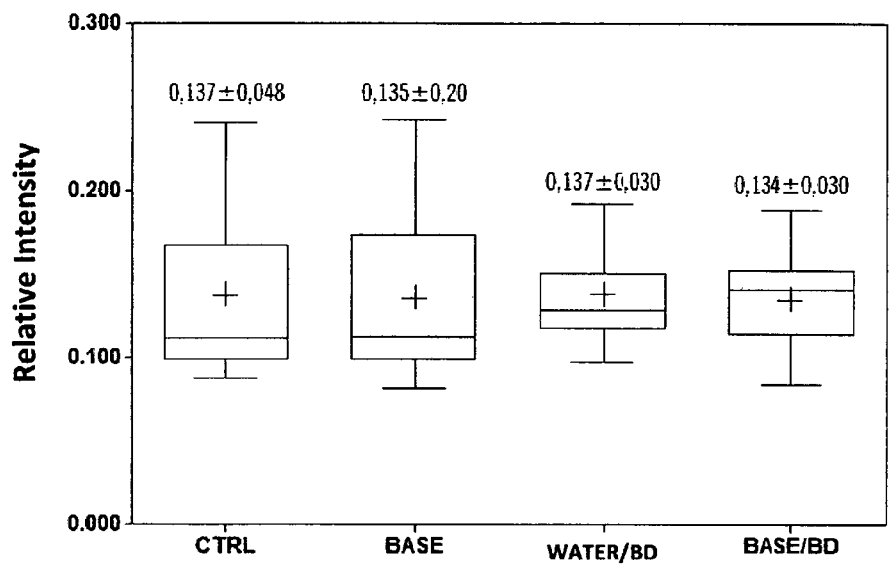
FIG. 1C shows average basal values obtained for each study group, for the parameter CT.
Figure 2A:
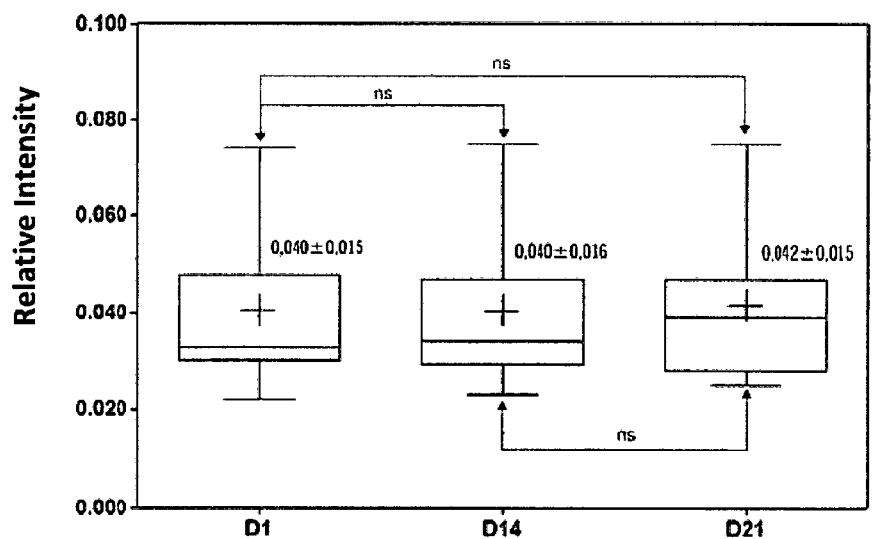
FIG. 2A shows results for the parameter Ort, control group.
Figure 2B:
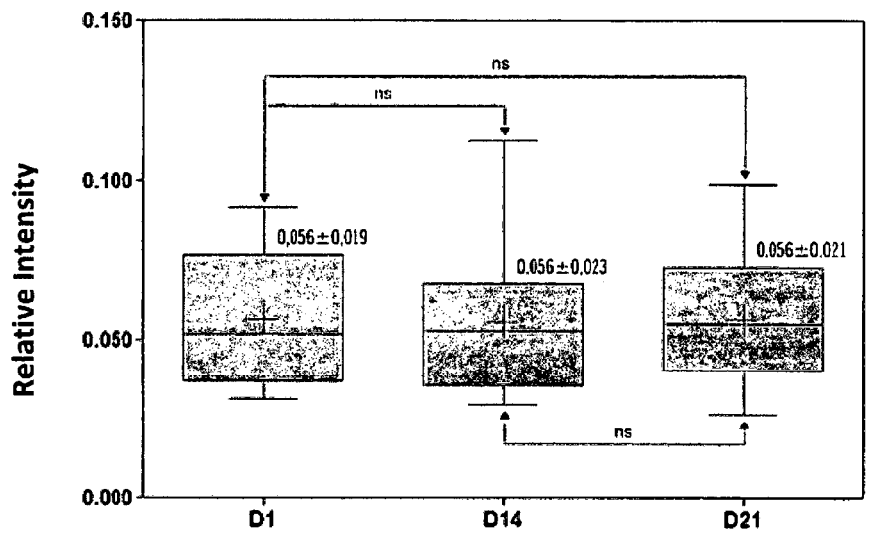
FIG. 2B shows results for the parameter Hex, control group.
Figure 2C:
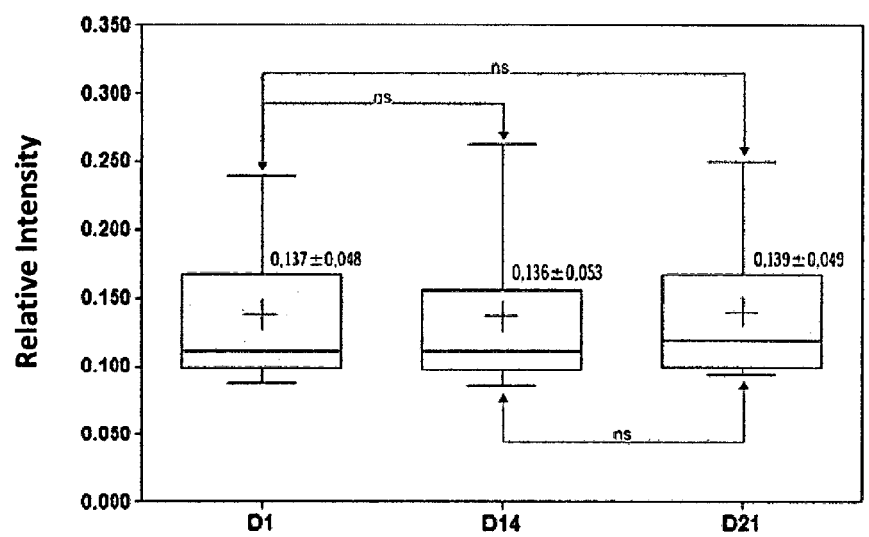
FIG. 2C shows results for the parameter CT, control group.
Figure 2D:
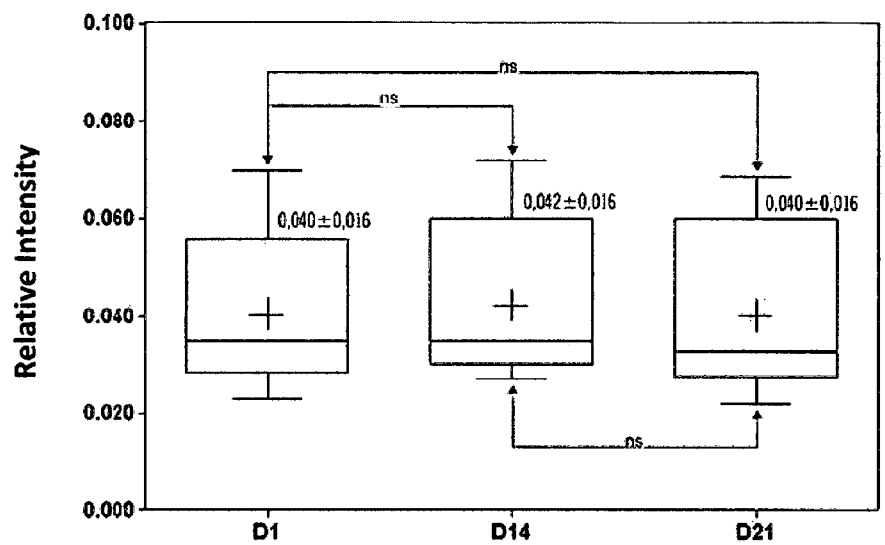
FIG. 2D shows results for the parameter Ort, BASE Group.
Figure 2E:
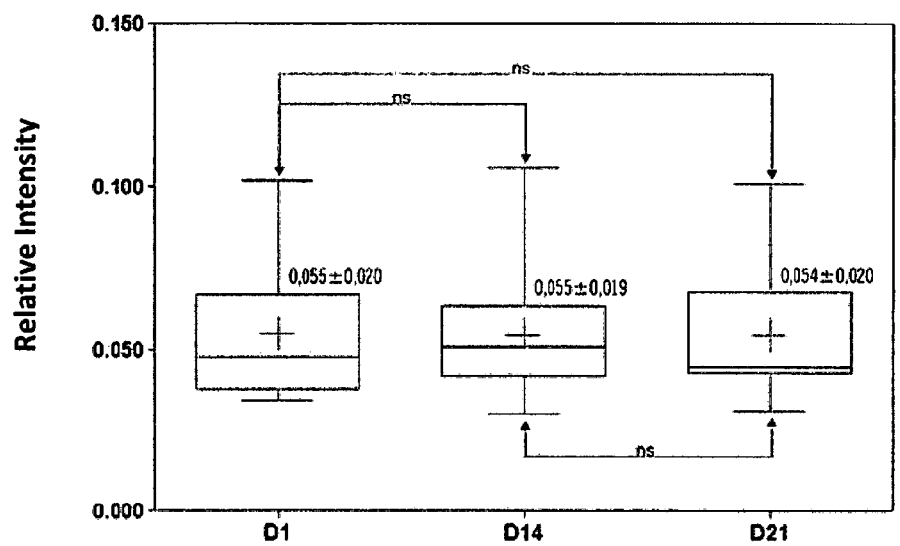
FIG. 2E shows results for the parameter Hex, BASE Group.
Figure 2F:
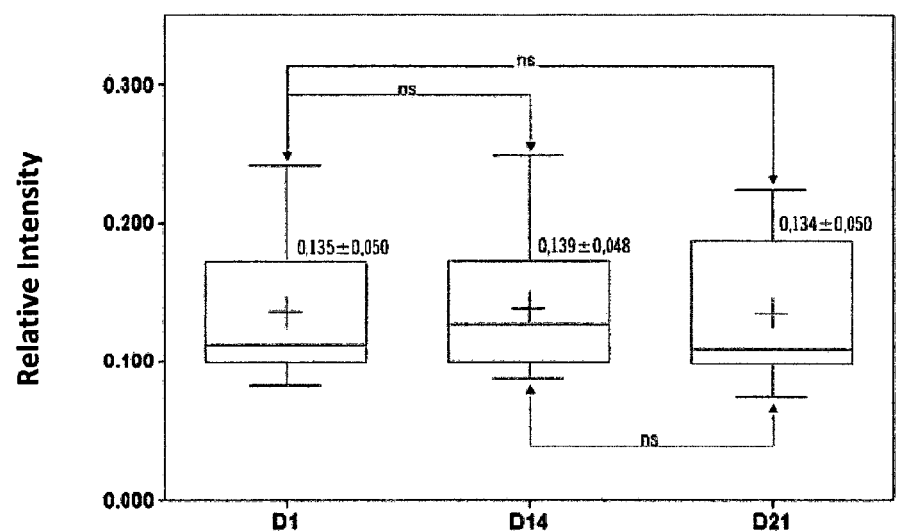
FIG. 2F shows results for the parameter CT, BASE Group.
Figure 2G:
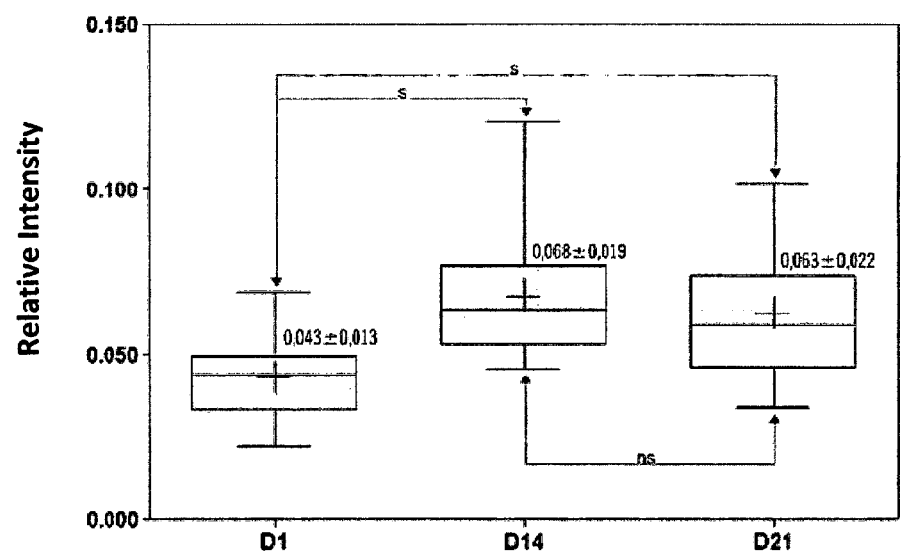
FIG. 2G shows results for the parameter Ort, WATER/BD Group.
Figure 2H:
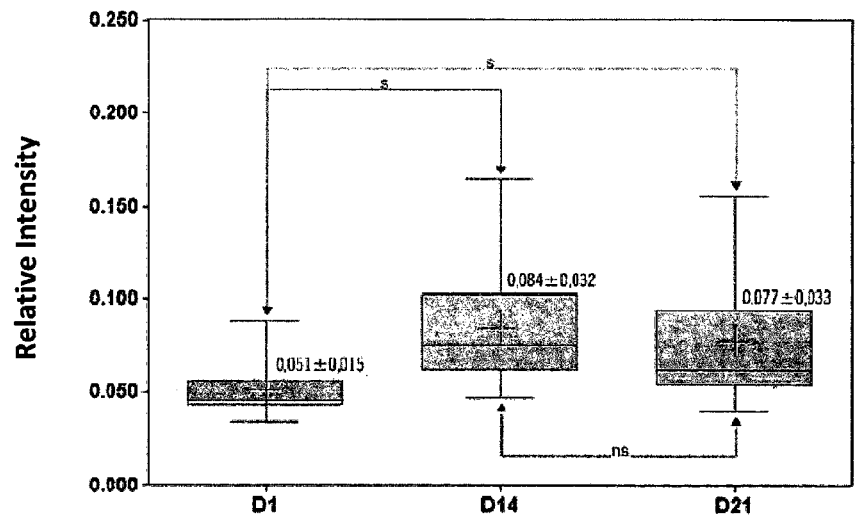
FIG. 2H shows results for the parameter Hex, WATER/BD Group.
Figure 2I:
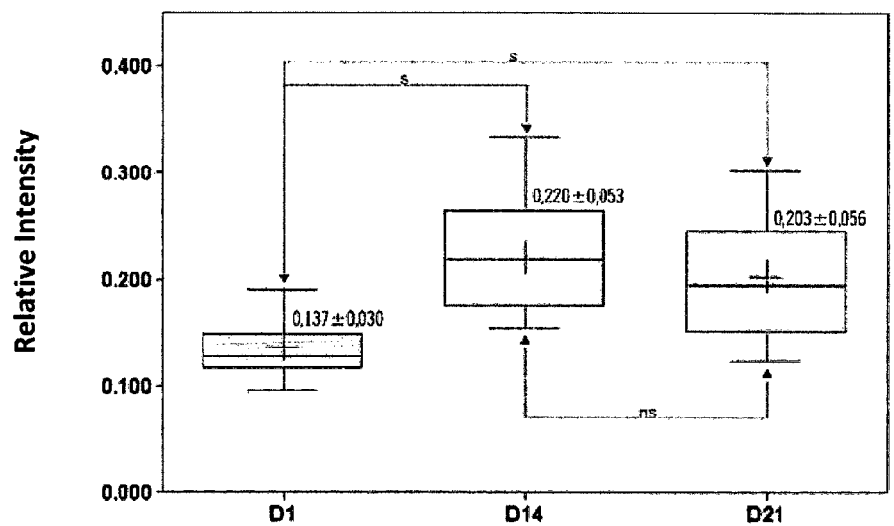
FIG. 2I shows results for the parameter CT, WATER/BD Group.
Figure 2J:
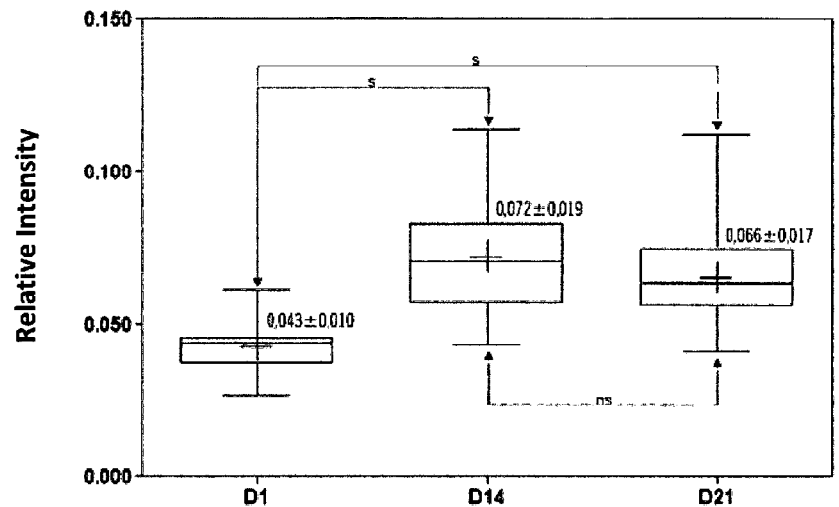
FIG. 2J shows results for the parameter Ort, BASE Group/BD.
Figure 2K:
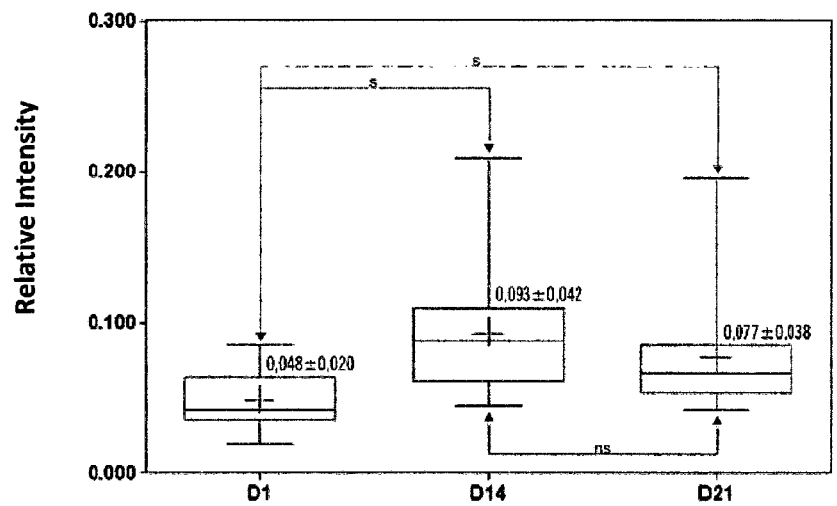
FIG. 2K shows results for the parameter Hex, BASE Group/BD.
Figure 2L:
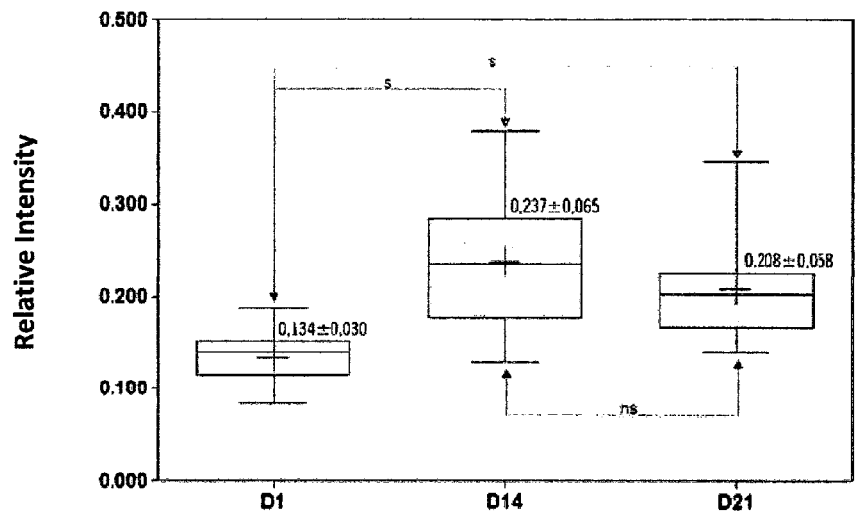
FIG. 2L shows results for the parameter CT, BASE Group/BD.
Figure 3A:
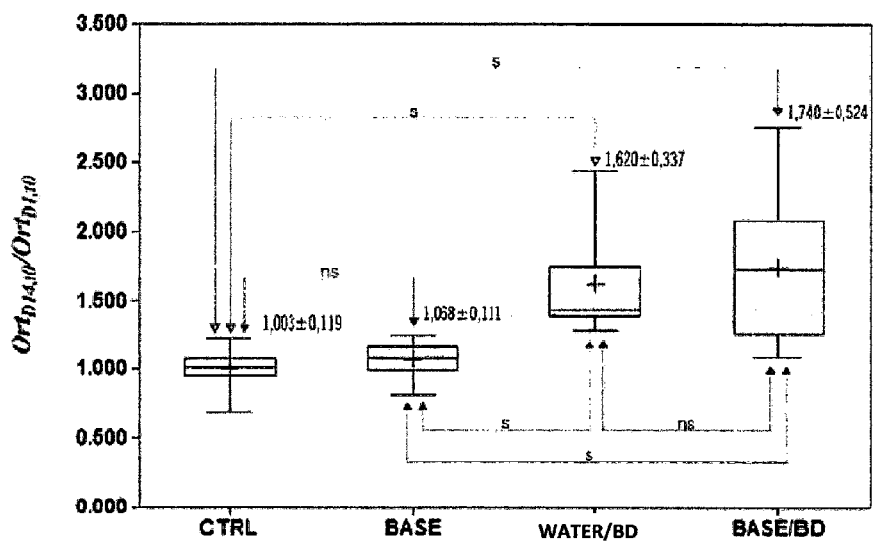
FIG. 3A shows a comparison between study groups, parameter Ort, D14.
Figure 3B:
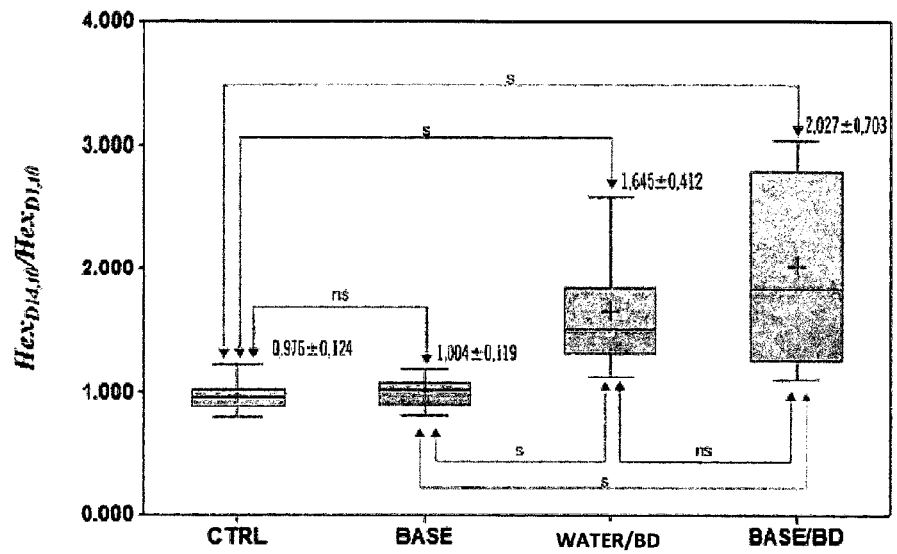
FIG. 3B shows a comparison between study groups, parameter Hex, D14.
Figure 3C:
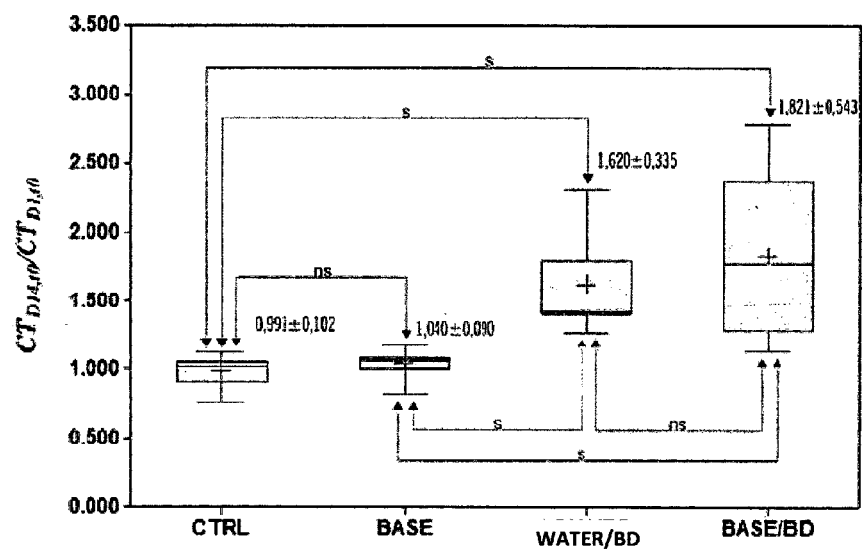
FIG. 3C shows a comparison between study groups, parameter CT, D14.
Figure 3D:
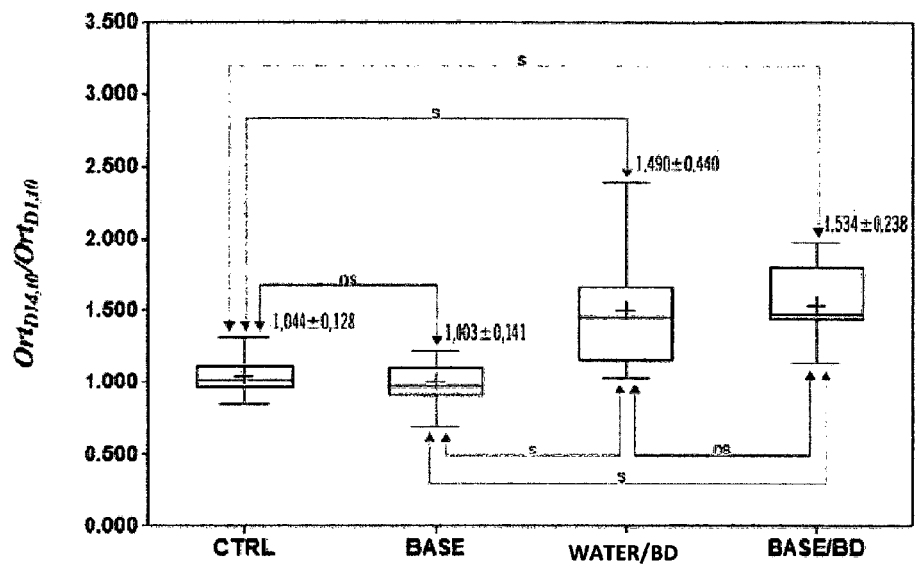
FIG. 3D shows a comparison between study groups, parameter Ort, D21.
Figure 3E:
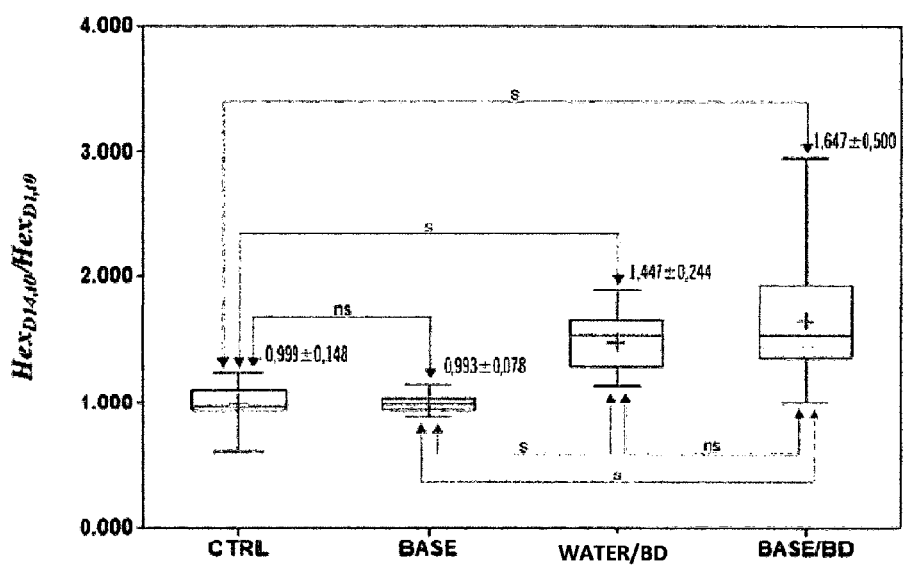
FIG. 3E shows a comparison between study groups, parameter Hex, D21.
Figure 3F:
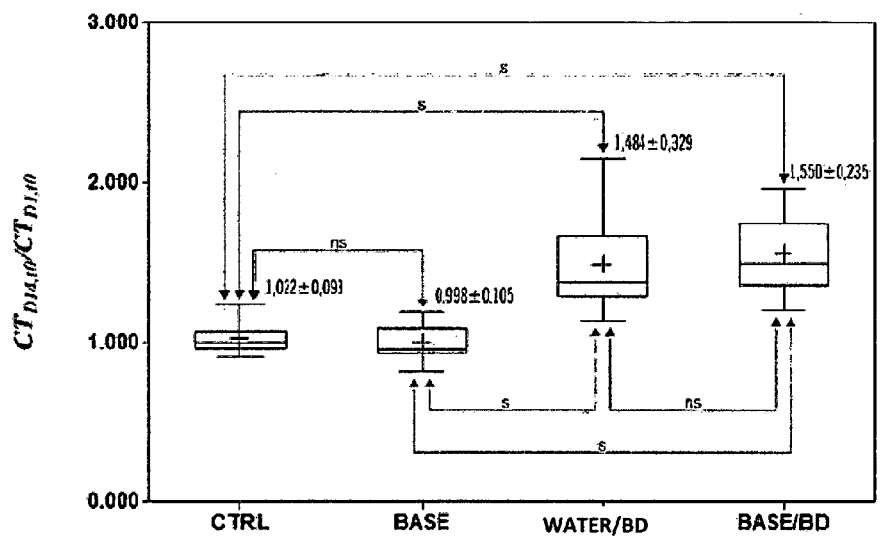
FIG. 3F shows a comparison between study groups, parameter CT, D21.

The average basal values obtained for the Ort, Hex and CT parameters, for each study group, illustrated in FIGS. 1A, 1B and 1C, were compared with each other to determine whether the study groups began under the same initial conditions. Accordingly, the method of single factor variance analysis was used, with the Tukey post-hoc test, considering a confidence interval of 95%: $F_{D1, t0, P}$ vs. $F_{D1, t0, P^1}$ F=(Ort, Hex, CT; P, P$^1$)=different study groups, including CONTROL, BASE, WATER/BD, BASE/BD).

The results of the statistical evaluation demonstrate that there was no statistically significant difference between the average values of the parameters evaluated for the study groups.

This result indicated that the study was begun under equal conditions among the study groups. Evaluating the alterations of the parameters during the course of the study in t0.

The average values obtained for the Ort, Hex and CT parameters during the course of the study are illustrated in FIGS. 2A-2L.

For statistical evaluation, the single factor variance analysis method was used, repeated data, with the Tukey post-hoc test, considering a confidence interval of 95%: $F_{D1, t0, P}$ vs. $F_{Di, t0, P}$ F=(Ort, Hex, CT; i,j=1, 14, 21, i≠j; P=study group).

In accordance with the results obtained for the CONTROL and BASE groups, there were no significant modifications for the Ort, Hex and CT parameters during the period of study. This outcome indicated that the natural variations in the crystalline fractions present in the lamellar layers of the stratum corneum were not significant and also that the use of the Base Cream did not promote significant alterations.

In the groups treated with the composition according to the present invention in concentration of 5% by weight in relation to the total weight of the composition, dispersed in water (WATER/BD group) or in the base cream (BASE group/BD), there were significant increases in the average values of the Ort, Hex and CT parameters after 14 days of use (D14 in relation to D1).

After the period of 7 days of washout (D21, interrupted use), although the values of the parameters decreased, they still remained significantly higher that the basals prior to treatment (D1).

These results indicated that the treatment with the composition according to the present invention, dispersed in water or in the cosmetic base, was capable of increasing the fraction of the crystalline phase with orthorhombic packing in relation to the initial state. The same effect was noted in relation to the hexagonal phase and in relation to the total crystallinity, indicating a reduction of the liquid lamellar phase.

Comparison Between the Study Groups at Each Stage of the Study in t0

The comparison between the average basal values obtained for each parameter, group and stage of the study (14 days of treatment, D 14, and 7 days of washout, D21) was carried out using the ratios between the parameters in the times D14 or D21 and the initial values, D1. The values calculated are illustrated in FIGS. 3A-3F. The statistical analysis was carried out using the single factor variance analysis method, with the Tukey post-hoc test, considering a confidence interval of 95% $(F_{D1, t0}/F_{D1,t0})_P$ vs. $(F_{D1, t0}/F_{D1,t0})_P^1$ F=(Ort, Hex, CT; i=14, 21; P, P$^1$=different study groups).

In accordance with the results obtained, after the 14 days of the stage of use of the products, there was no statistically significant difference between the BASE group and the CONTROL group, considering the three parameters evaluated, Ort, Hex and CT. This result indicated that the Base Cream caused no significant alteration in the crystalline structure of the lamellar phase of the stratum corneum of the skin of the volunteers treated. The same result was noted after the period of seven days of suspension of use.

In the case of the group of volunteers treated with the composition according to the present invention, in concentration of 5% by weight in water, WATER/BD Group, or incorporated in concentration of 5% by weight in the Base cream, BASE group/BD, after 14 days of treatment, there was a significant increase in the relative average values of the Ort, Hex and CT parameters, both in relation to the CONTROL group and to the BASE group.

This result indicated that these products were efficient in increasing the crystallinity of the lamellar phase of the corneum extract, considering the orthorhombic and hexagonal structures.

After seven days of suspended treatment, the results for the WATER/BD and BASE/BD groups still remained significantly higher in relation to the CONTROL and BASE groups, indicating a long-lasting effect during the period considered.

There was no statistically significant difference between the WATER/BD and BASE/BD groups considering the values obtained for the Ort, Hex or CT parameters after the 14 days of treatment (D14) or the 7 days of suspension of use (D21).

Overall Comparison Between the Study Groups in t0

An overall comparison between study groups, for each parameter, was carried out considering the results obtained in t0 during the course of all the stages of the study, that is D1, D14 and D21.

Accordingly, considering the value curves of the parameters during the course of the study (y: $F_{t0}$; x: $D_1$) (F=Ort, Hex, CT; i=1, 14 or 21), the parameter area on the curve, $AUC_{F,t0}$, was calculated for each volunteer used in the statistical comparison between the study groups. $AUC_{t0=14}$ [$(F_{D14, t0}+F_{D1, t0})/2$]7[(FD21, t0+FD14, t0)]/2–21 ($F_{D1, t0}$).

Figure 4A:
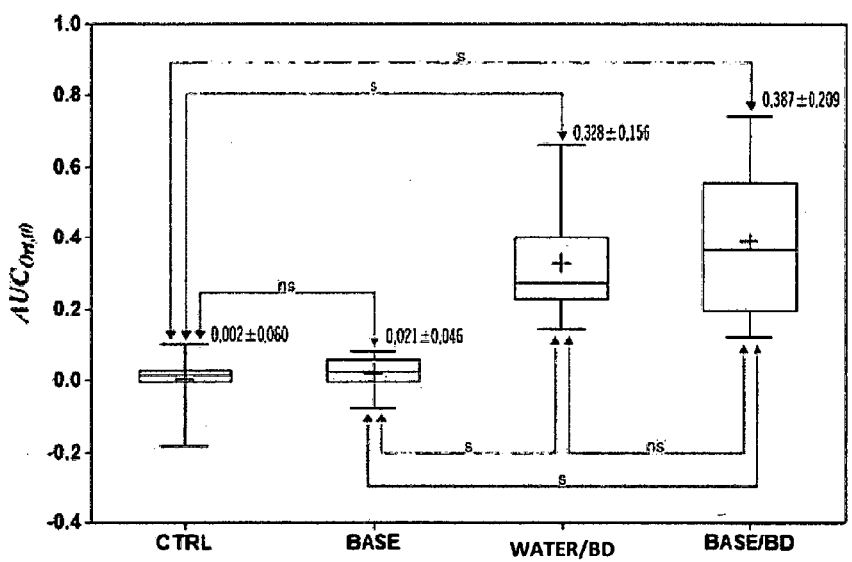
FIG. 4A shows an overall comparison between study groups, parameter Ort.
Figure 4B:
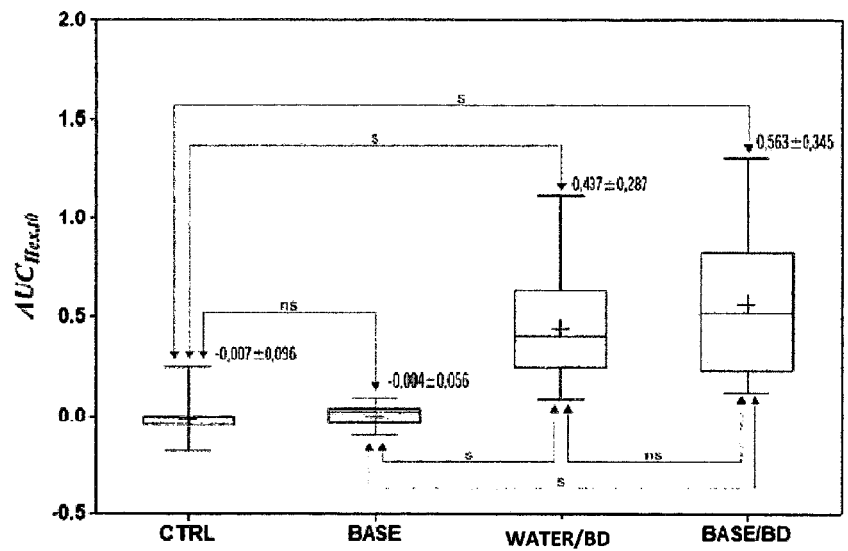
FIG. 4B shows an overall comparison between study groups, parameter Hex.
Figure 4C:
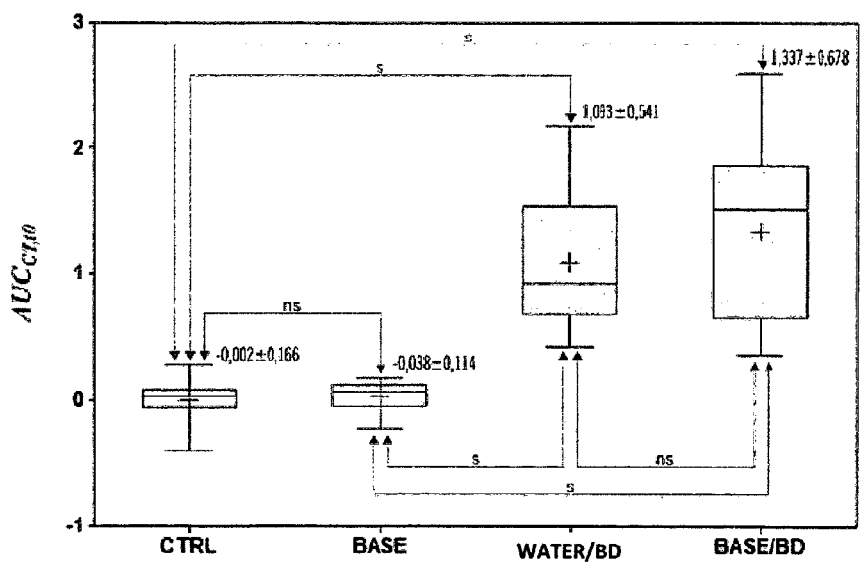
FIG. 4C shows an overall comparison between study groups, parameter CT.

The AUC $_{F, t0}$ values calculated are illustrated in FIGS. 4A-4C. The statistical analysis was carried out using the single factor variance analysis method, with the Tukey post-hoc test, considering a confidence interval of 95%: $AUC_{F,t0, P}$ vs. $AUC_{F,t0, P}^1$(F–Ort, Hex, CT; P, P$^1$=different study groups).

In accordance with the results obtained, for the Ort, Hex or CT parameters, there was no statistically significant difference between the overall results of the CONTROL and BASE groups, again indicating that the treatment with the Base Cream did not promote significant alterations in the crystalline fractions of the lamellar layers of the stratum corneum.

However, the groups treated with the composition according to the present invention, in an amount of 5% by weight in water, WATER/BD group, or 5% by weight in the Base Cream, BASE group/BD, present cumulative effects during the course of the treatment, including the period of suspension of the use, significantly higher than the CONTROL and BASE groups for the three parameters.

This result indicated that the active ingredient provided a significant increase effect in the fractions of the crystalline orthorhombic and hexagonal structures.

Figure 5A:
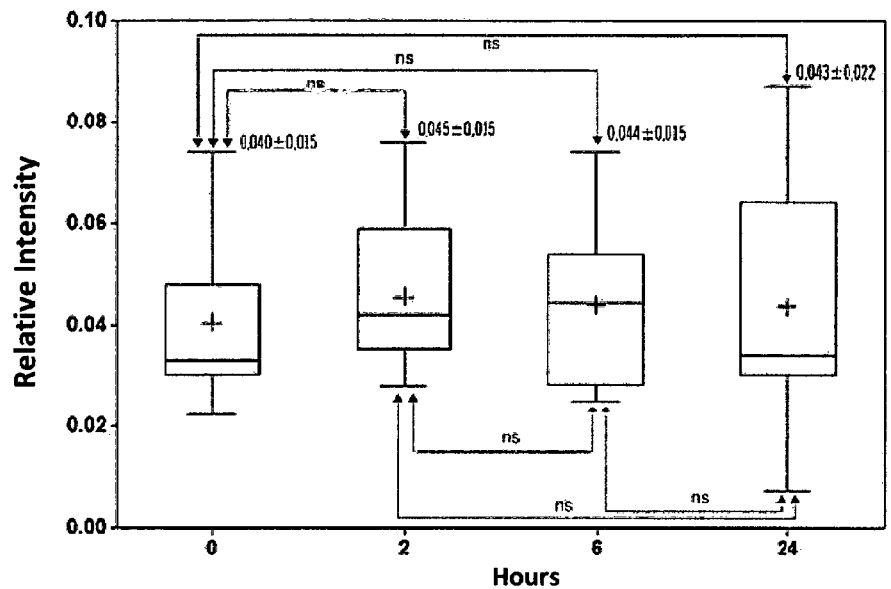
FIG. 5A shows kinetics for parameter Ort, control group, D1.
Figure 5B:
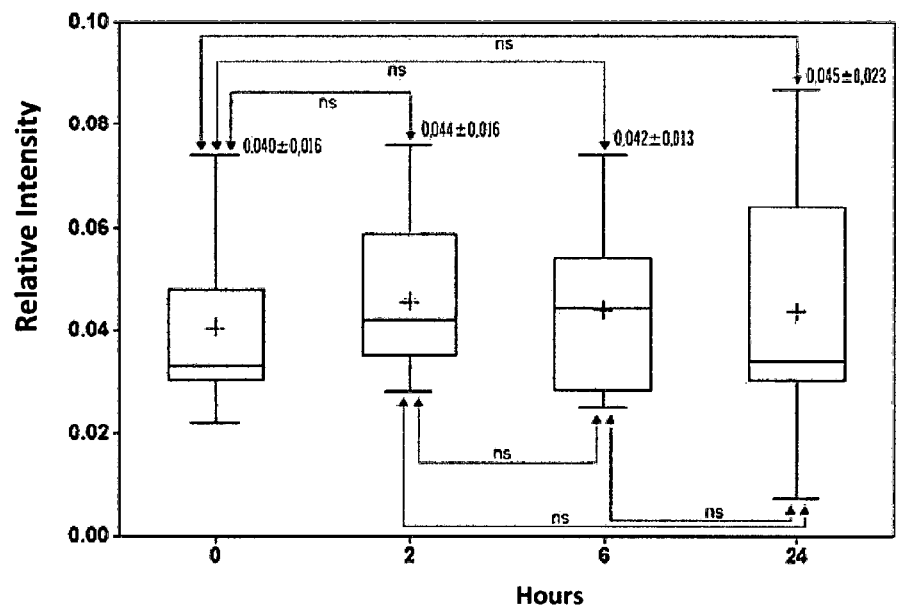
FIG. 5B shows kinetics for parameter Ort, control group, D14.
Figure 5C:
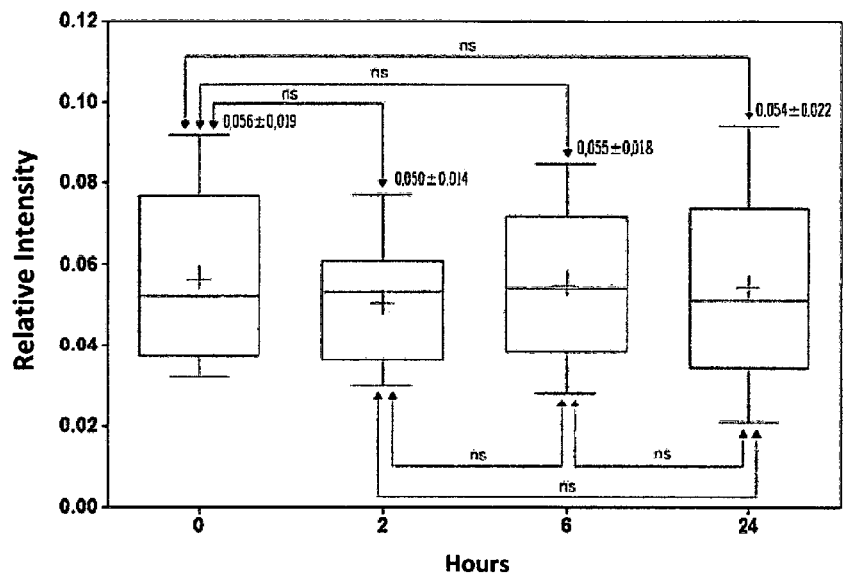
FIG. 5C shows kinetics for parameter Hex, control group, D1.
Figure 5D:
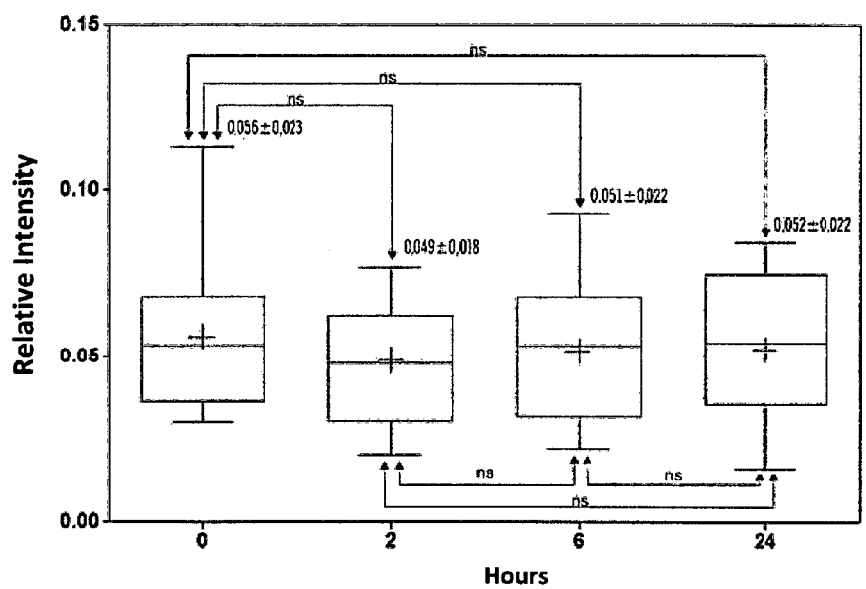
FIG. 5D shows kinetics for parameter Hex, control group, D14.
Figure 5E:
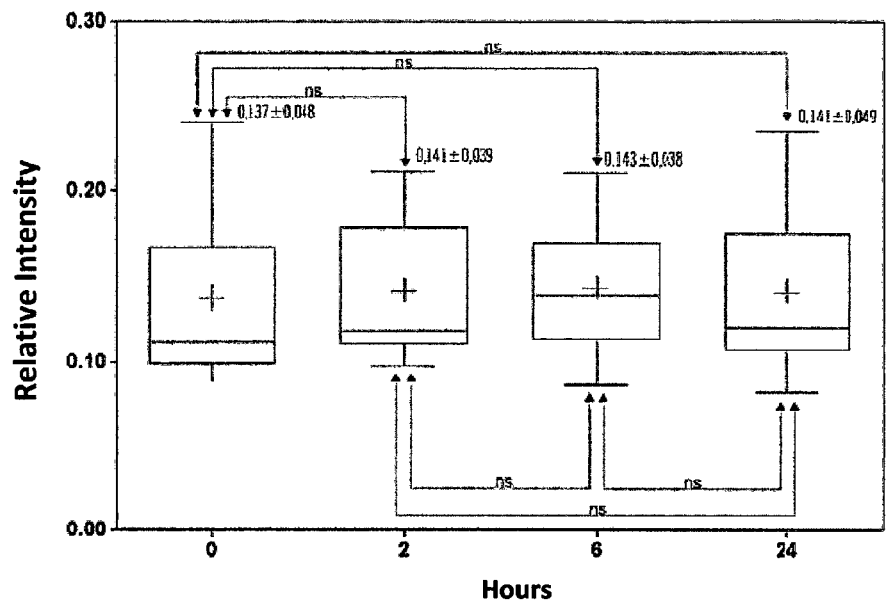
FIG. 5E shows kinetics for parameter CT, control group, D1.
Figure 5F:
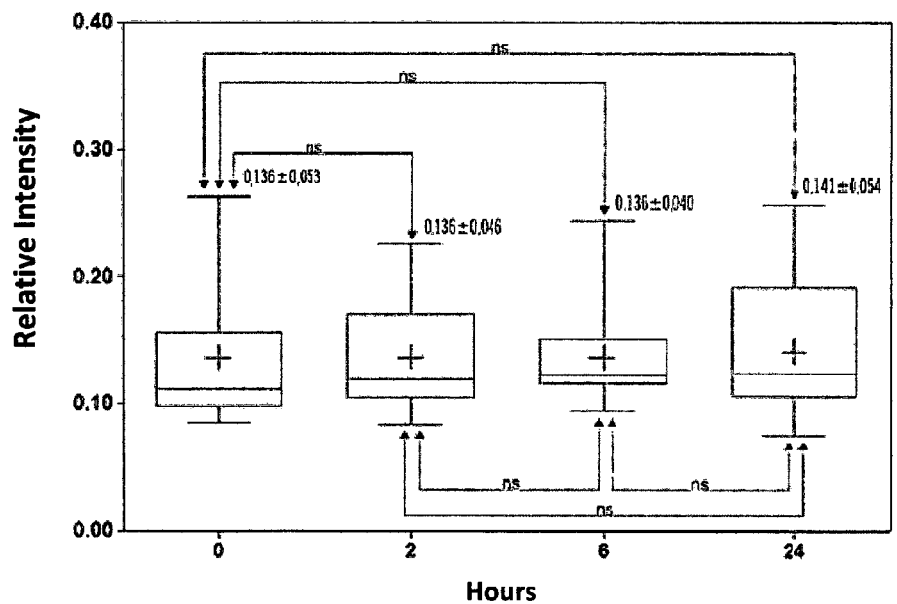
FIG. 5F shows kinetics for parameter CT, control group, D14.
Figure 5G:
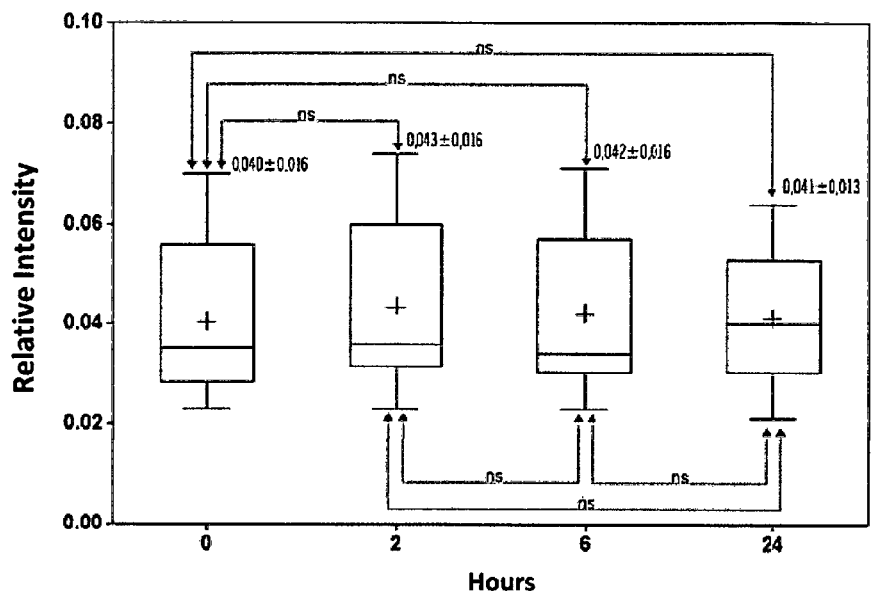
FIG. 5G shows kinetics for parameter Ort, BASE group, D. The value x=0h represents the initial status of the skin, the others, after applying the product.
Figure 5H:
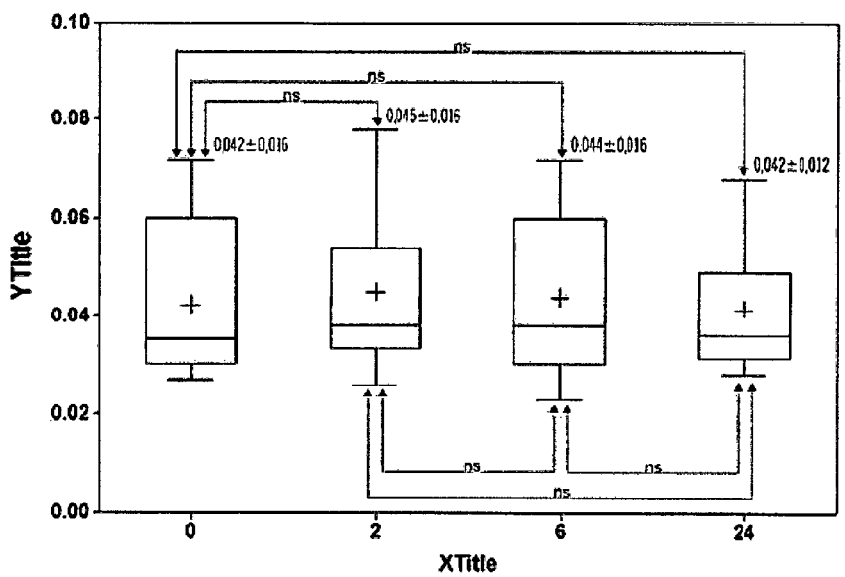
FIG. 5H shows kinetics for parameter Ort, BASE group, D14. The value x=0h represents the initial status of the skin, the others, after applying the product.
Figure 5I:
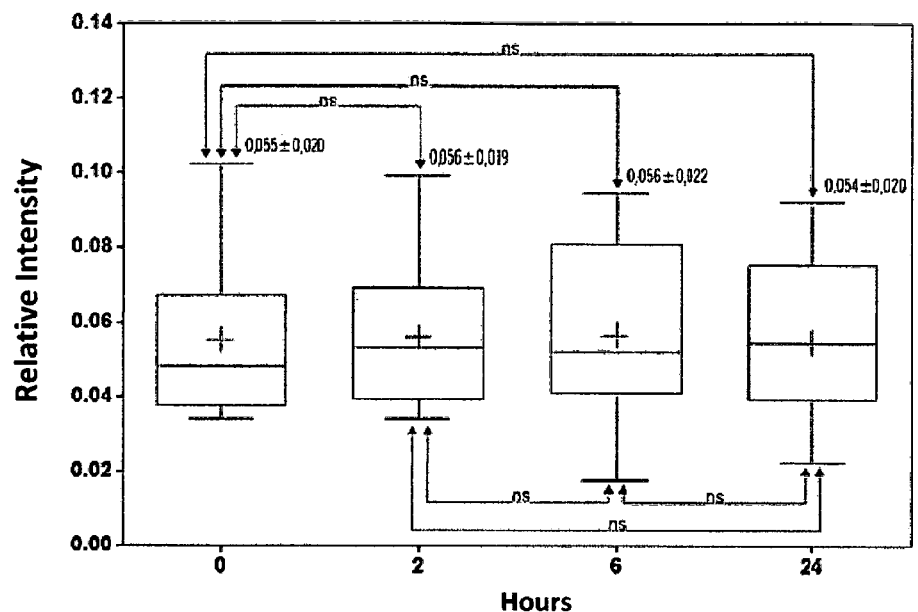
FIG. 5I shows kinetics for parameter Hex, BASE group, D1. The value x=0h represents the initial status of the skin, the others, after applying the product.
Figure 5J:
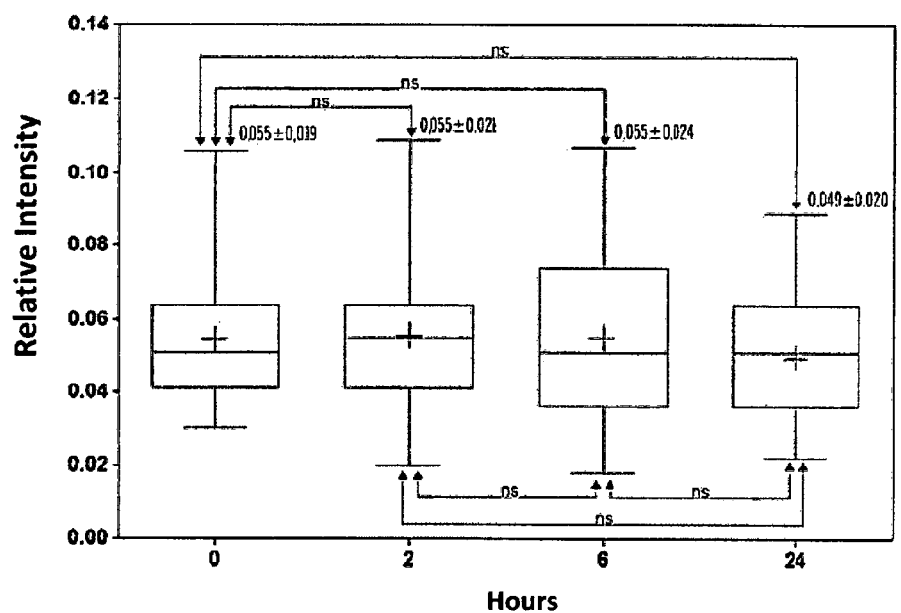
FIG. 5J shows kinetics for parameter Hex, BASE group, D14. The value x=0h represents the initial status of the skin, the others, after applying the product.
Figure 5K:
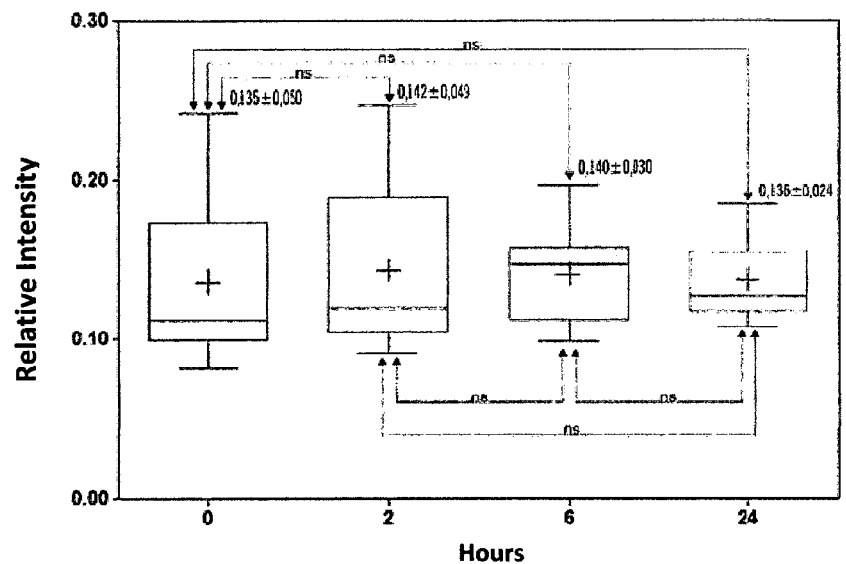
FIG. 5K shows kinetics for parameter CT, BASE group, D1. The value x=0h represents the initial status of the skin, the others, after applying the product.
Figure 5L:
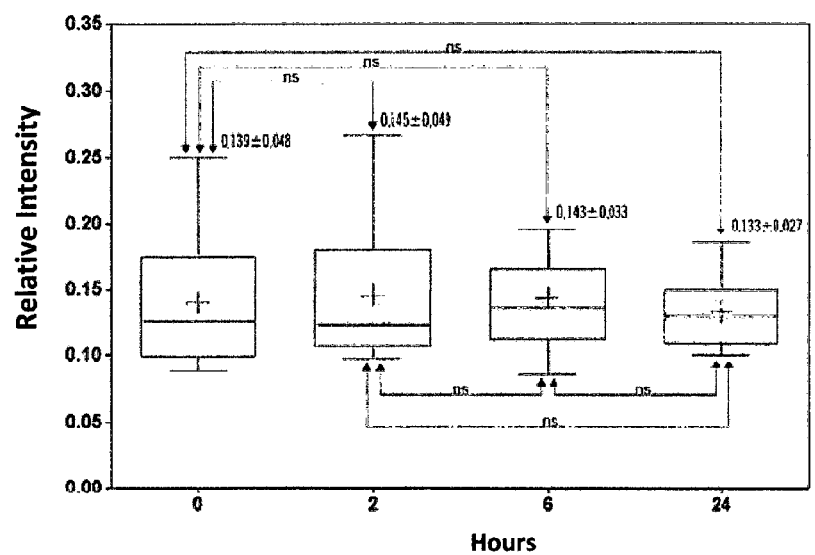
FIG. 5L shows kinetics for parameter CT, BASE group, D14. The value x=0h represents the initial status of the skin, the others, after applying the product.
Figure 5M:
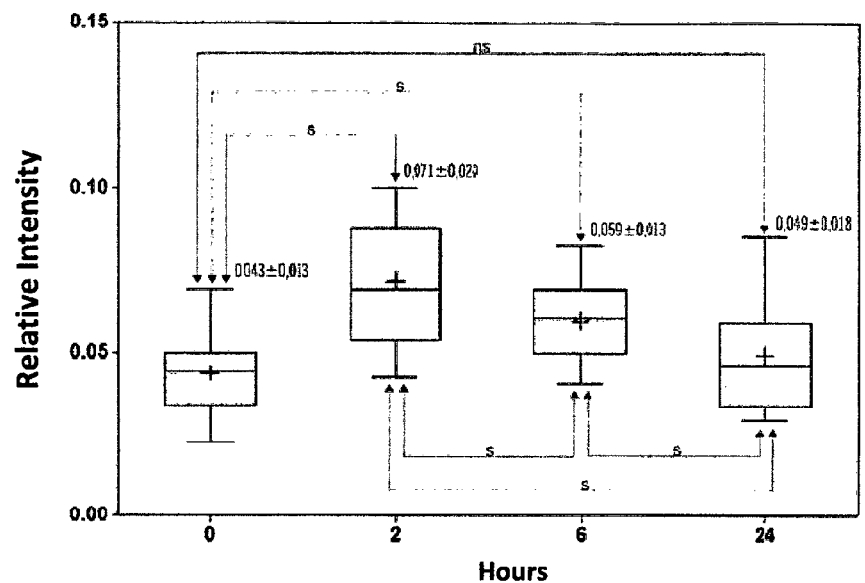
FIG. 5M shows kinetics for parameter Ort, WATER/BD group, D1. The value x=0h represents the initial status of the skin, the others, after applying the product.
Figure 5N:
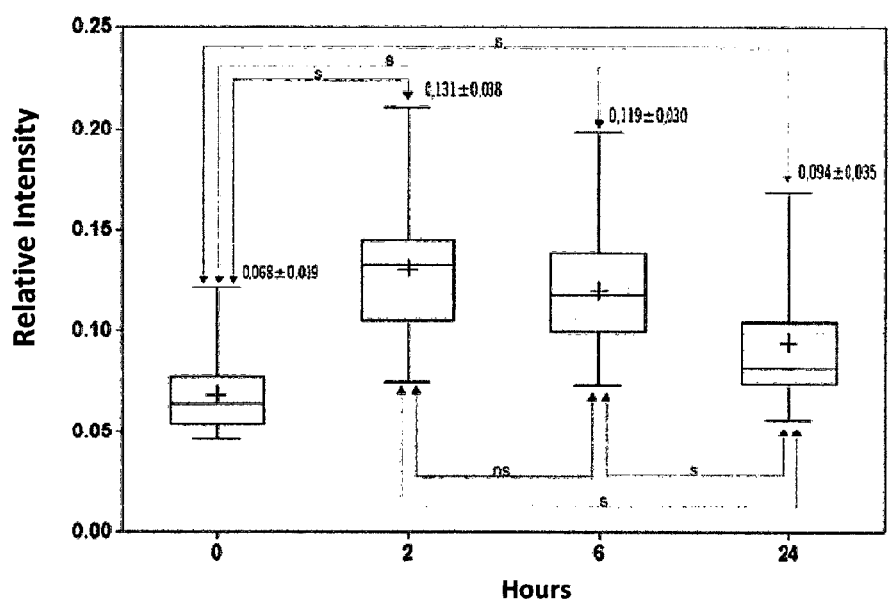
FIG. 5N shows kinetics for parameter Ort, WATER/BD group, D14. The value x=0h represents the initial status of the skin, the others, after applying the product.
Figure 5O:
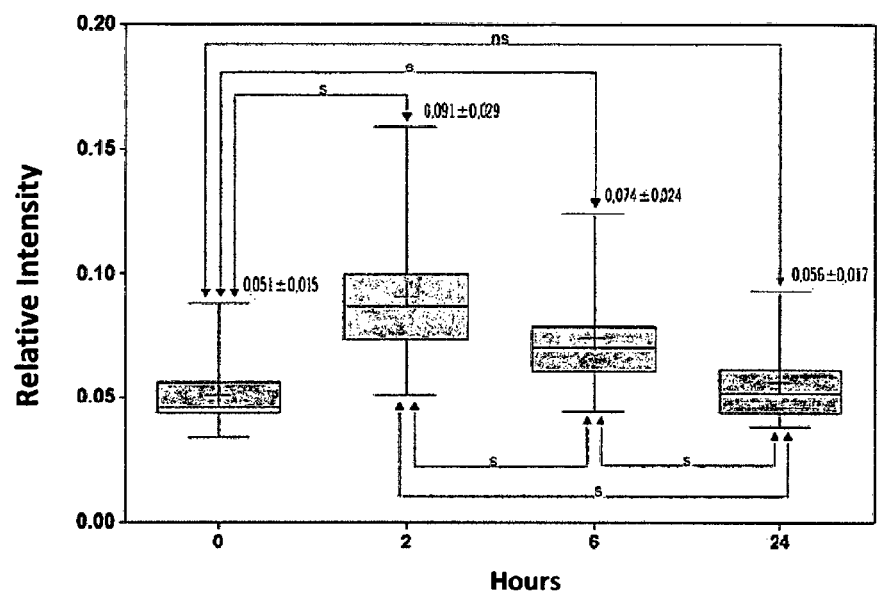
FIG. 5O shows kinetics for parameter Hex, WATER/BD group, D1. The value x=0h represents the initial status of the skin, the others, after applying the product.
Figure 5P:
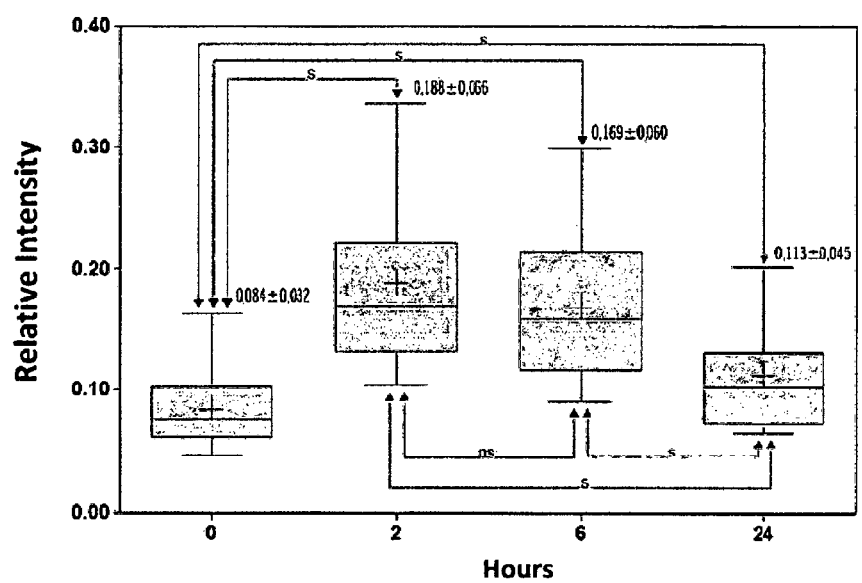
FIG. 5P shows kinetics for parameter Hex, WATER/BD group, D14. The value x=0h represents the initial status of the skin, the others, after applying the product.
Figure 5Q:
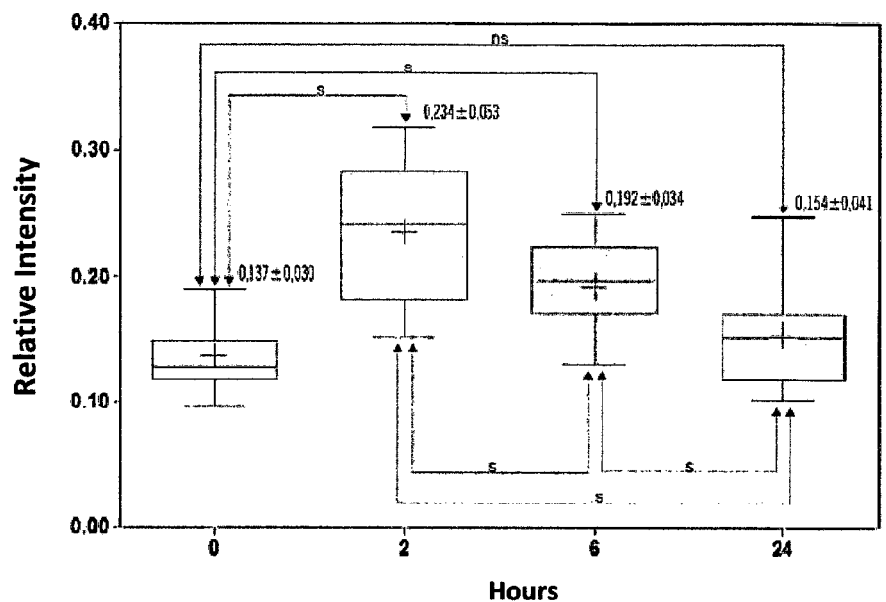
FIG. 5Q shows kinetics for parameter CT, WATER/BD group, D1. The value x=0h represents the initial status of the skin, the others, after applying the product.
Figure 5R:
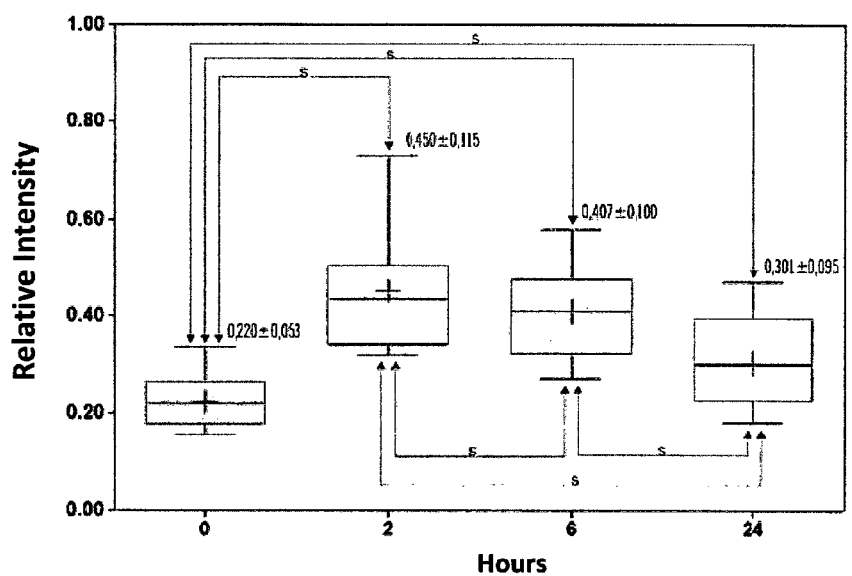
FIG. 5R shows kinetics for parameter CT, WATER/BD group, D14. The value x=0h represents the initial status of the skin, the others, after applying the product.
Figure 5S:
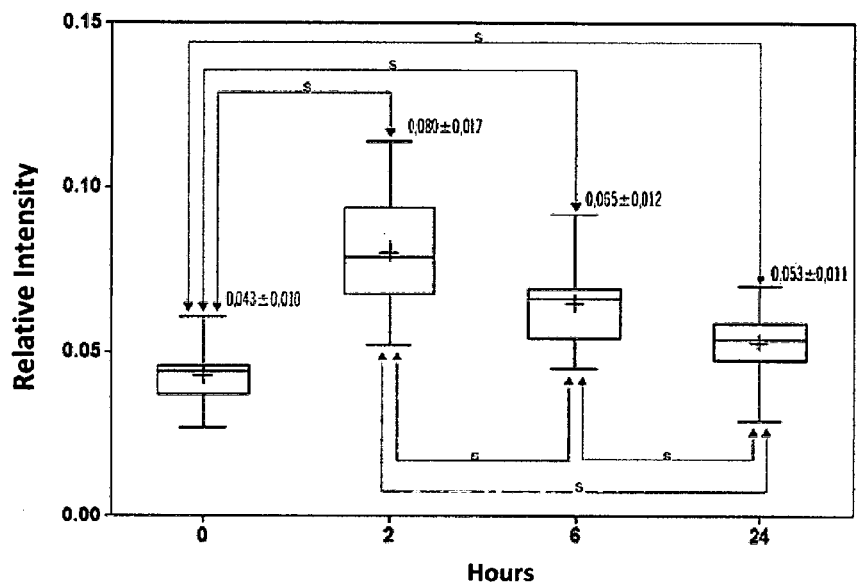
FIG. 5S shows kinetics for parameter Ort, BASE group/BD, D1. The value x=0h represents the initial status of the skin, the others, after applying the product.
Figure 5T:
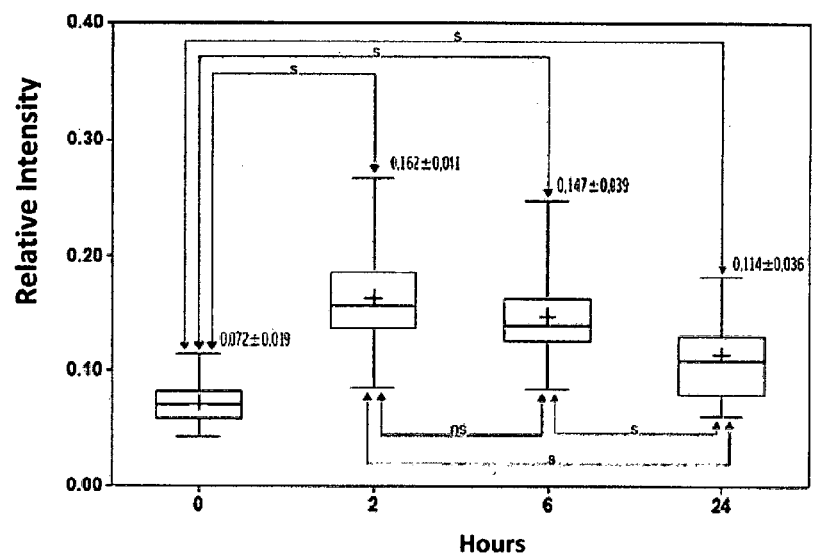
FIG. 5T shows kinetics for parameter Ort, BASE group/BD, D14. The value x=0h represents the initial status of the skin, the others, after applying the product.
Figure 5U:
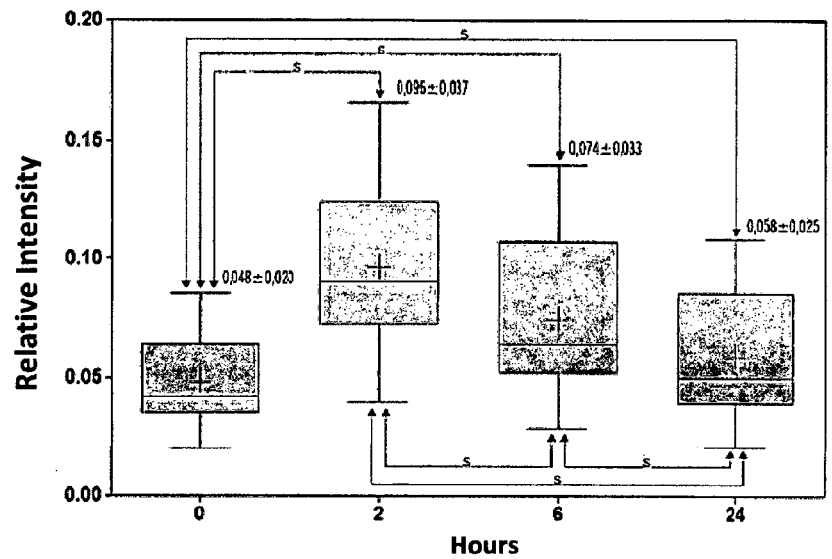
FIG. 5U shows kinetics for parameter Hex, BASE group/BD, D1. The value x=0h represents the initial status of the skin, the others, after applying the product.
Figure 5V:
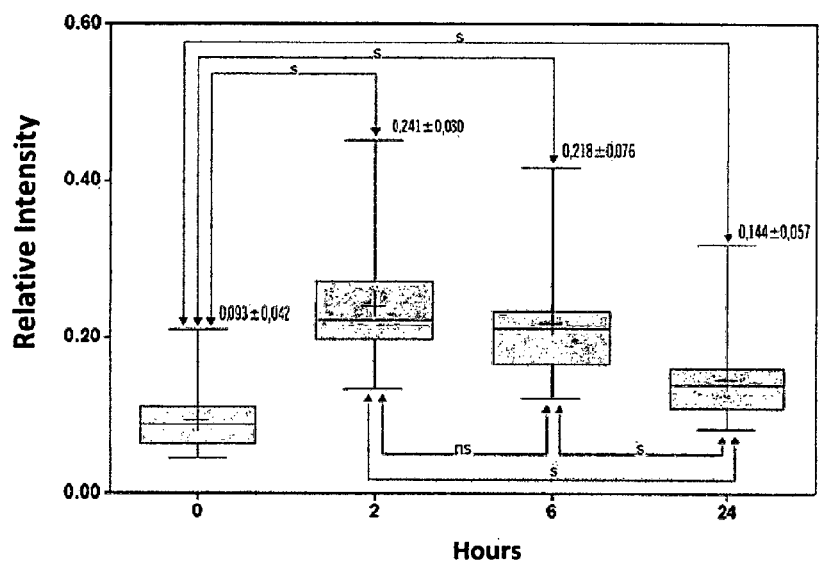
FIG. 5V shows kinetics for parameter Hex, BASE group/BD, D14. The value x=0h represents the initial status of the skin, the others, after applying the product.
Figure 5X:
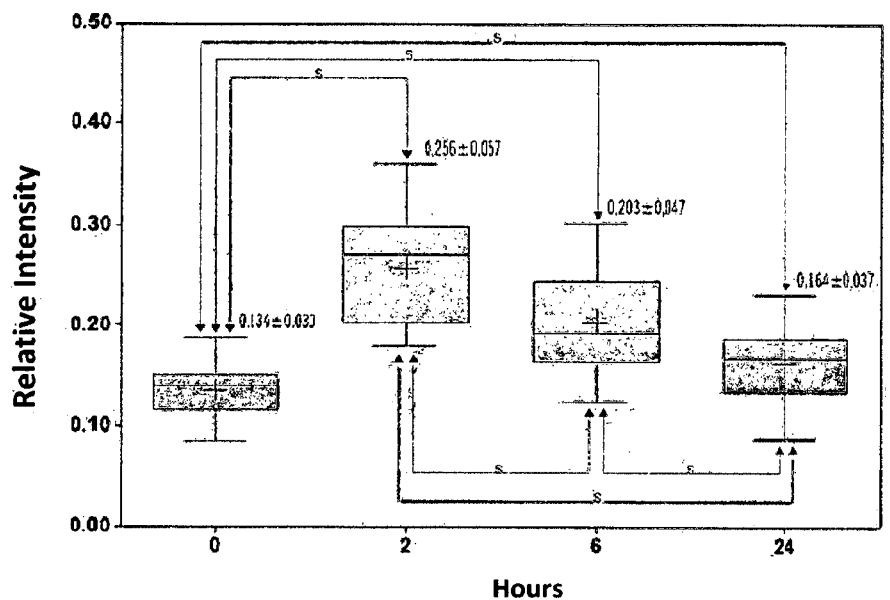
FIG. 5X shows kinetics for parameter CT, BASE group/BD, D1. The value x=0h represents the initial status of the skin, the others, after applying the product.
Figure 5Z:
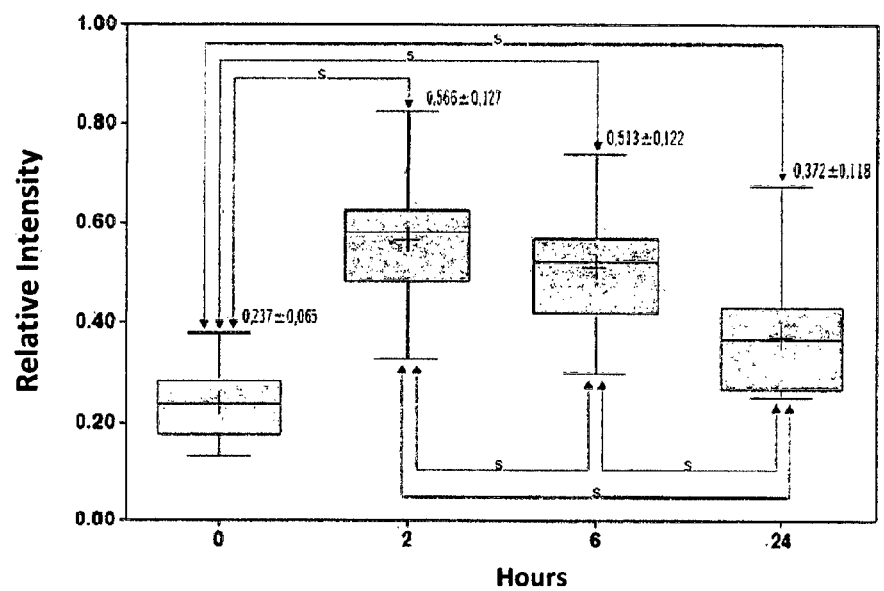
FIG. 5Z shows kinetics for parameter CT, BASE group/BD, D14. The value x=0h represents the initial status of the skin, the others, after applying the product.
Figure 6A:
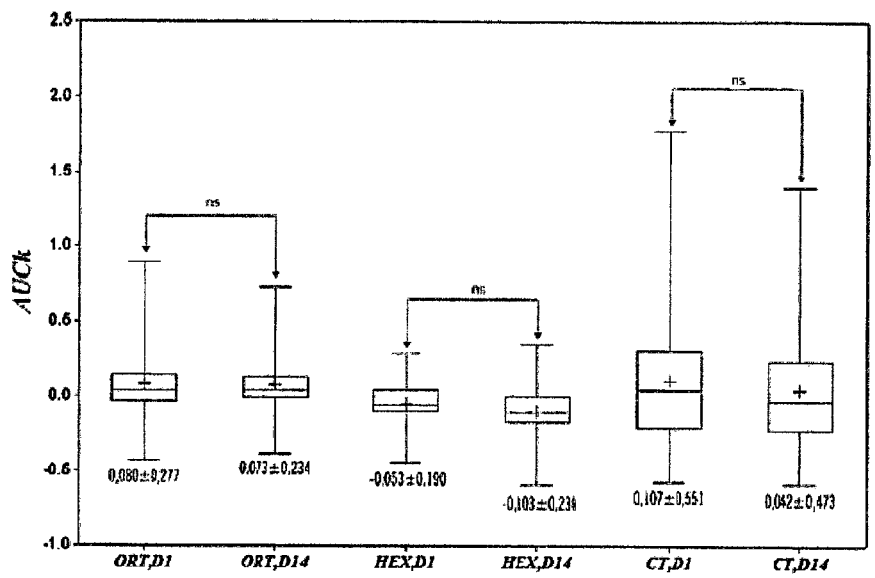
FIG. 6A shows AUCk values, a comparison between kinetics D1 and D14, control group.
Figure 6B:
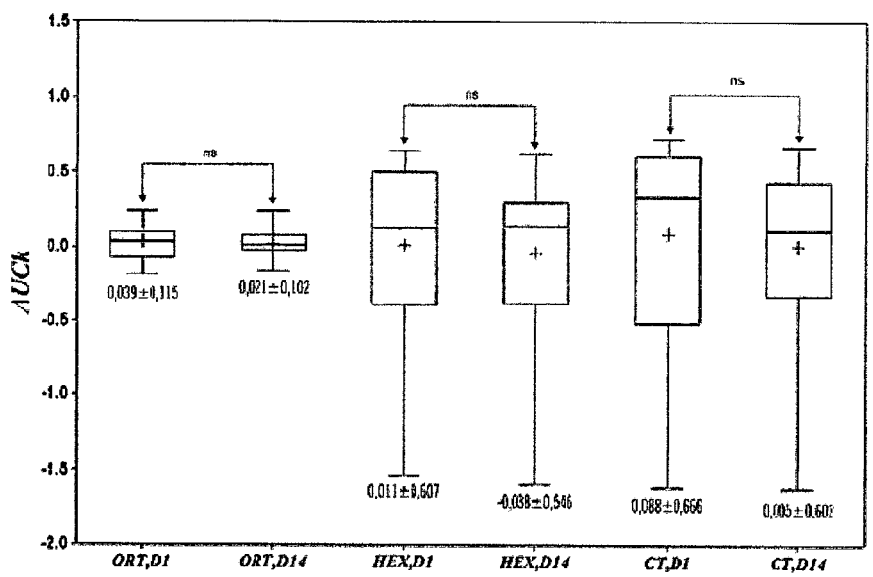
FIG. 6B shows AUCk values, a comparison between kinetics D1 and D14, BASE group.
Figure 6C:
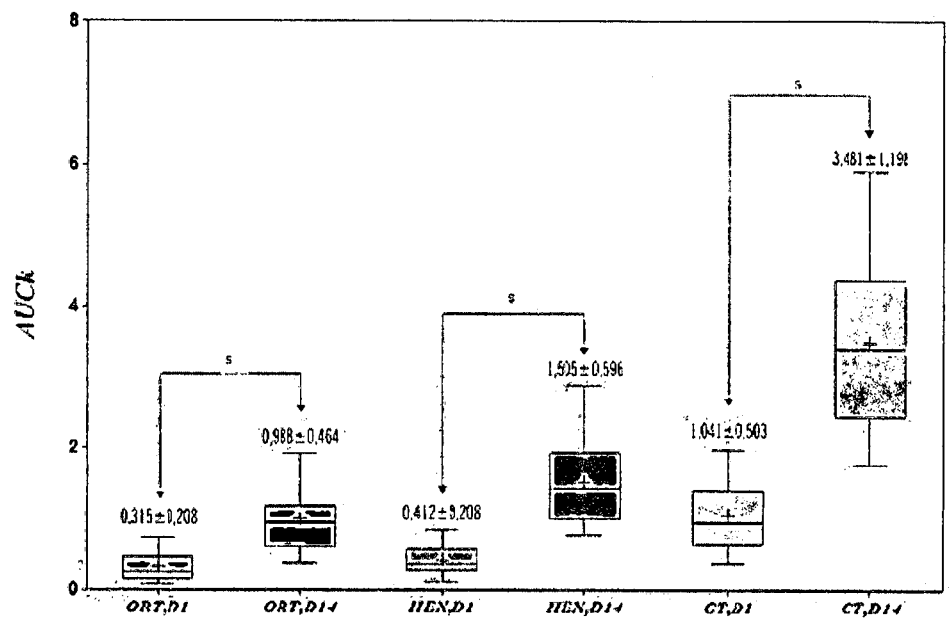
FIG. 6C shows AUCk values, a comparison between kinetics D1 and D14, WATER/BD group.
Figure 6D:
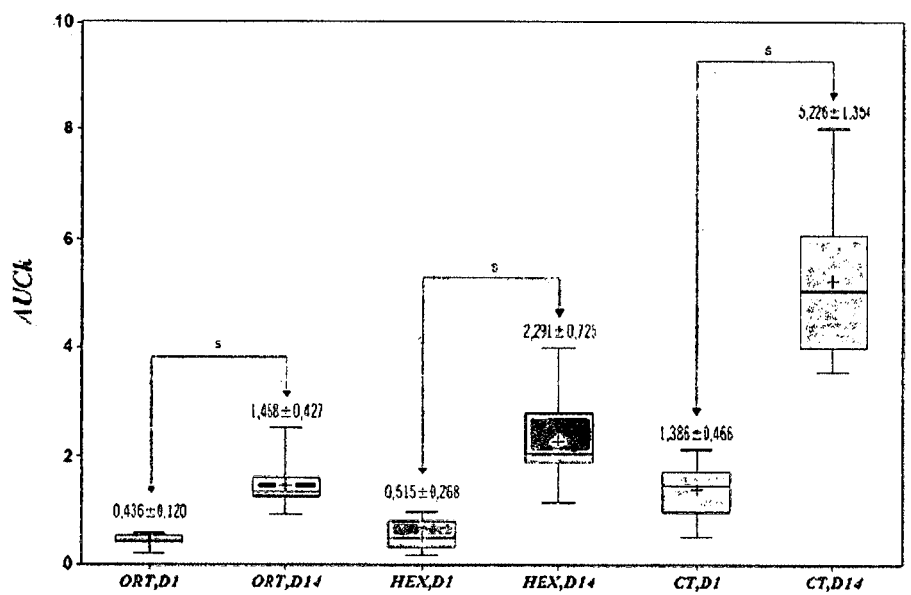
FIG. 6D shows AUCk values, a comparison between kinetics D1 and D14, BASE group/BD.

There was no statistically significant difference between the results achieved for the WATER/BD and BASE/BD groups, considering the three parameters evaluated. Evaluating the kinetics of alterations of the parameters per group and stage of the study The data obtained for each parameter, 2, 6 and 24 hours after applying the products, in relation to the basal, t0, for the stages of the study D1 and D14, are illustrated in FIGS. 5A-5Z.

The statistical evaluations of the kinetics were carried out using the single factor variance analysis method, with the Tukey post-hoc test, considering a confidence interval of 95%: $F_{Di, tj}$ vs. $F_{Di,tk}$ (F=Ort, Hex, CT; i=D14, D21; j≠k, j, k=0, 2, 6, 24 h).

In accordance with the results obtained for the CONTROL group, no significant variations in the average values of the Ort, Hex and CT parameters were noted on the first day of the study or after the period of 14 days, based on the evaluation time (0, 2, 6 and 24 h).

In the case of the group treated with the base cream (BASE), on the first day of the study on which the volunteers had first contact with the product, no significant variations were noted in the average values of the Ort, Hex and CT parameters, in the evaluation times after applying the product (2, 6 and 24 h) in relation to the initial average values of the skin (0h or t0). This result, relating to kinetics after the first contact with the product, indicated that the product caused no significant alteration in the fractions of the crystalline phases of the lamellar layers of the stratum corneum.

After 14 days of continued use of the Base Cream, having redone the kinetics study, no significant alterations were noted in the initial skin parameters (t0, 24 hours after the latest application of the Base Cream), 2, 6, or 24 hours after a fresh application of the product. This result indicated that the continued use of the Base Cream product for 14 days did not change the way in which the skin reacted to contact with the product, in terms of alterations in the crystalline fractions.

In the kinetics of the first day of the study for the WATER/BD group, a significant increase was noted in the average initial values of the Ort, Hex and CT parameters, 2 hours after applying the product. Six (6) hours after application, there was a decrease in the average values of the parameters in relation to the prior time (2 h), but they still remained significantly higher than the initial ones. Twenty-four (24) hours after application, there was a further reduction in the average values of the parameters, there being no statistical difference in relation to the respective initial values, indicating the return of the skin to the initial condition prior to applying the product. This result indicated that soon after first contact with the product, there was a significant alteration of the skin, with an increase in the total crystallinity and in the fractions of the crystalline orthorhombic and hexagonal phases. However, after 24 hours, the skin returned to its initial conditions.

After 14 days of continued use of the composition according to the present invention in 5% by weight in water, WATER/BD group, having redone the kinetics study, 2 hours after applying the product, a significant increase was noted in the Ort, Hex and CT parameters in relation to the initial condition of the skin, measured 24 hours after the latest application of the period of use of 14 days (the average values of the parameters in D14, t0 were significantly higher than those obtained in D1, t0). Six (6) hours after application, the amounts continued to be significantly higher than the initial amounts and, twenty-four (24) hours after application, even with a reduction in the average values, they still remained significantly higher than the respective initial values.

This result indicated that the continued use of the product caused not only an alteration in the basal condition of the skin, as seen previously, but also prolonged the immediate effects of applying the product, at an interval of 24 h.

In the kinetics of the first day of the study for the BASE group/BD, a significant increase was noted in the average initial values of the Ort, Hex and CT parameters, 2 hours after applying the product. Six (6) hours after applying the product, there was a decrease in the average values of the parameters, but these still remained significantly higher than the initial values. Twenty-four (24) hours after application, there was another reduction in the average values of the parameters, yet the average values remained significantly higher than the initial values. This result indicated that soon after first contact with the product there was a significant alteration of the skin, with an increase in the total crystallinity and in the fractions of the crystalline orthorhombic and hexagonal phases, the effect being significant up to 24 hours after application.

After 14 days of continued use of the composition according to the present invention in an amount of 5% by weight in the Base Cream, BASE group/BD, having redone the kinetics study, 2 hours after applying the product, a significant increase of the Ort, Hex and CT parameters was noted in relation to the initial condition of the skin, measured 24 hours after the latest application of the period of use of 14 days (the average values of the parameters in D14, t0 were significantly higher than those obtained in D1, 0). Six (6) hours after application, the values continued to be significantly higher than the initial ones and 24 hours after application, even with a reduction in the average values, they still remained significantly higher that the respective initial values.

This result indicated that the continued use of the product caused not only an alteration in the basal condition of the skin, as seen previously, but also prolonged the immediate effects of applying the product, at a 24-hour interval.

Comparison Between the Kinetics on the First Day of the Study and After 14 Days of Continued Use of the Products The comparison between the kinetic curves obtained on the first day of the study, relating to the first contact of the skin with the product, and after 14 days of continued use, was established by calculating the parameter area on the kinetic curves, $AUCk_{F,Di,P} = 2[(F_{Di,t2,P} - F_{Di,t0,P})/2] + 18(F_{Di,t24,P} - F_{Di,t6,P})/2] - 24 - F_{Di,t0,P})$ wherein: F=Ort, Hex, CT; i=1,14 days; P=study group).

The values calculated for the parameter AUCk are illustrated in FIGS. 6A to 6D, indicating the average behavior of the product during the "immediate" post-application evaluation of the product, in an interval of up to 24 hours.

The statistical evaluation was carried out using the t-Student test method, paired (by volunteer), bimodal, considering a confidence interval of 95%, applied at $AUCk_{F,D14,P}$ vs. $AUCk_{F,D1,P}$.

In accordance with the results from the statistical analysis for the CONTROL and BASE groups, there were no significant differences between the kinetics obtained in D1 and D14, indicating that there were no natural alterations of the skin or caused by the application of the Base Cream, in terms of the crystalline fractions of the lamellar layers of the stratum corneum studied.

In the case of the groups treated with the composition according to the present invention in an amount of 5% by weight in water, WATER/BD group, or 5% by weight in the Base Cream, BASE group, the kinetic curves taken after 14 days of continued use of the products obtained average values significantly higher than the respective kinetics seen on the first day of the state (first contact with the product). These results indicated that with the continued use of the products, there was a cumulative modification of the skin properties, such that the immediate reaction to the product, over 24 hours after application, was intensified.

Overall Comparison Between the Immediate Effects, or Kinetics, after Applying the Products, Considering 14 Days of Continued Use The overall comparison between the study groups, considering the modifications in the immediate effects of the products, or kinetic curves, 14 days after application was established by calculating, for each study group and parameter, the ratios $Rk = AUCk_{F,D14,P}/AUCk_{F,D1,P}$ (wherein F=Ort, Hex, CT; P=study group).

Figure 7A:
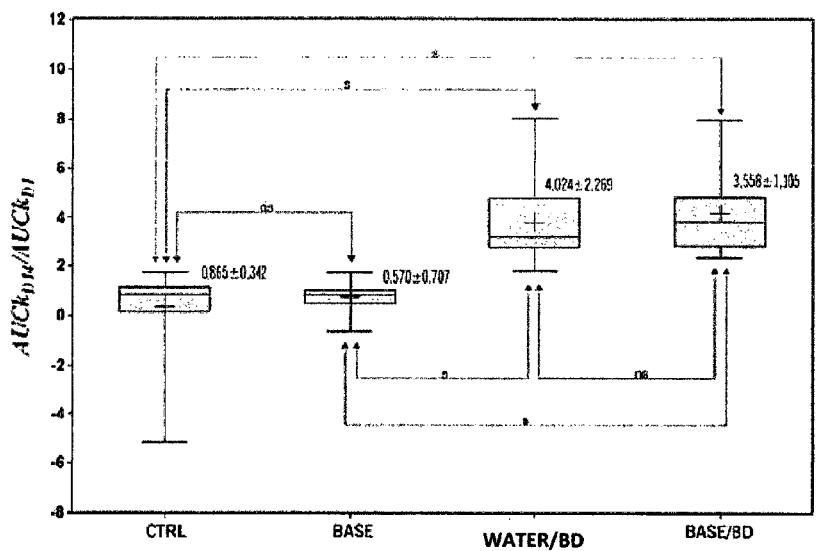
FIG. 7A shows Rk values, a comparison between kinetics of the products, parameter Ort.
Figure 7B:
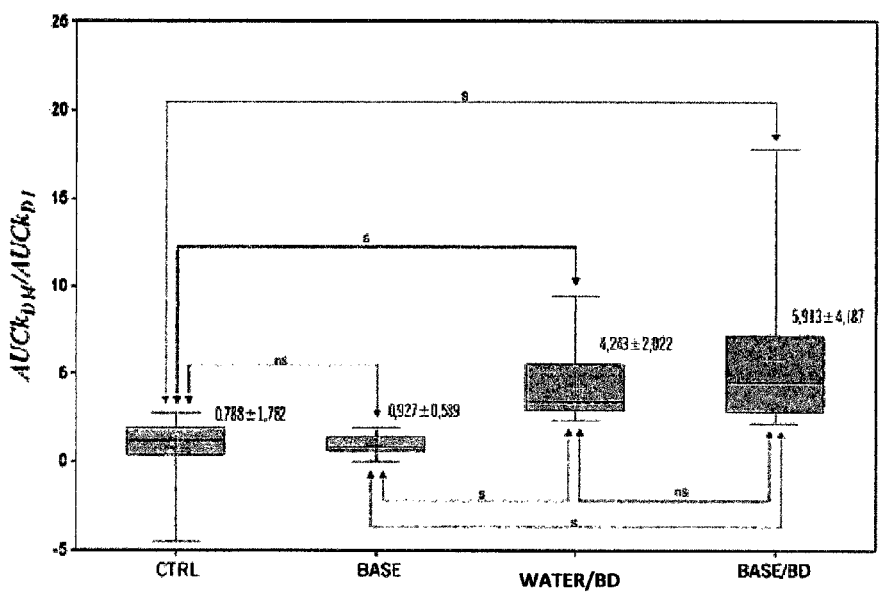
FIG. 7B shows Rk values, a comparison between kinetics of the products, parameter Hex.
Figure 7C:
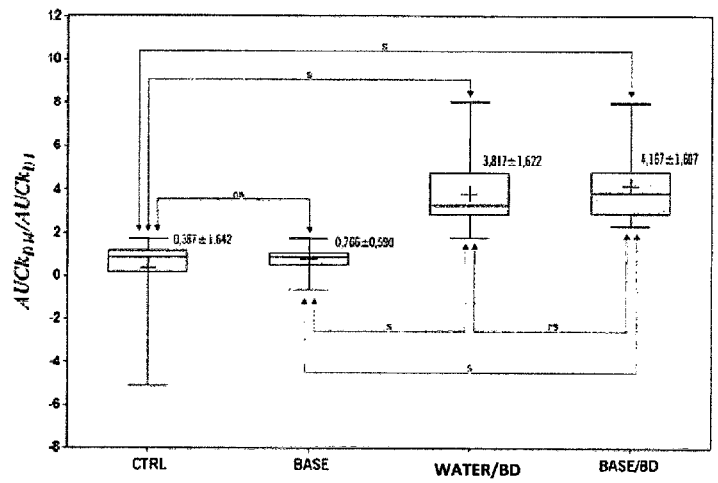
FIG. 7C shows Rk values, a comparison between kinetics of the products, parameter CT.

The values calculated are illustrated in FIGS. 7A-7C.

The statistical comparison was carried out using the single factor variance analysis method, with the Tukey post-hoc test, considering a confidence interval of 95%, applied to $Rk_{F,P}$ vs. $Rk_{F,P}^1$ (wherein F=Ort, Hex, CT; P, P$^1$=different study groups).

In accordance with the results obtained, there was no statistically significant difference between the results achieved in the CONTROL and BASE groups.

In contrast, in the WATER/BD and BASE/BD groups, there was no statistically significant difference, indicating that the composition according to the present invention, when carried in a base cream, maintains the same properties of the material in water.

Conclusion on the Results of the Tests Described Above

The studies described above evaluated the degree of modification in the fractions of the crystalline structures of the orthorhombic and hexagonal type, in addition to the total crystallinity of the lamellar layer, particularly based on treatment with the composition according to the present invention, the results being summarized below.

For the CONTROL group, which used no product, no significant modifications were noted in the fractions in the orthorhombic and hexagonal crystalline phases, or even in the total crystallinity, in any of the study stages.

In the case of the group of volunteers treated with the Base Cream (Sample A), no significant alterations were noted either in the crystallinity parameters in the first 24 hours after first contact with the product. Even after 14 days of continued use of the Base Cream, no significant alterations were noted on the skin, evaluated 24 hours after the latest application. When the kinetics was redone after the period of continued use, no significant modifications were noted in the skin either, indicating that there was no conditioning of the skin. In the readings taken after 7 days of suspension of use of the Base Cream (washout), no significant alterations were noted in the crystallinity parameters either.

In the case of the groups treated with the products containing the composition according to the present invention in an amount of 5% by weight in water (Sample B) or in the Base Cream (Sample C), there was a significant average increase in the fractions of the crystalline orthorhombic and hexagonal phases in relation to the initial state, in the first 2 and 6 hours after first contact with the products (peaking at 2 hours). After 24 hours, the skin returned to the initial condition.

After 14 days of continued use of the products containing the composition according to the present invention, on reevaluating the skin of the volunteers, 24 hours after the latest application, a significant average increase was noted in the orthorhombic and hexagonal fractions. Even after the period of suspension of the use of the products for 7 days, the relative average values of the orthorhombic and hexagonal fractions continued to be significantly higher than the average initial basal values measured on the first day of the study.

This result indicated that the continued use of products containing the composition according to the present invention provides an increase effect in the long-lasting crystallinity of the skin.

In reevaluating the kinetics of the immediate effect of the products containing the composition according to the present invention, evaluated after a period of 14 days of continued use, it was noted that the increases in the crystalline orthorhombic and hexagonal fractions, 2, 6 and 24 hours after reapplication, significantly surpass those noted in the first contact with the product (kinetics carried out on the first day of the study). Additionally, the values after 24 hours remained significantly higher than the basal values.

This result indicates that the continued use of these products, containing the composition according to the present invention, not only alters the properties of the skin, increasing the crystalline fractions, but also makes the effect immediate, evaluated up to 24 hours after application, more intense. Put otherwise, there was a progressive increase in the crystallinity of the skin owing to use and an intensification of the immediate response attained soon after applying the product (up to 24 hours).

No significant differences were noted between the groups treated with the composition according to the present invention, in an amount of 5% by weight in water (Sample B) or in the Base Cream (Sample C), indicating that there was no significant influence of the vehicle on the results achieved.

Generally, the increase in the total crystallinity, originating in the increase of the orthorhombic and hexagonal fractions, implies in an improvement of the barrier function of the stratum corneum, favoring the retention of natural humidity, decreasing the permeability of the stratum corneum.

The orthorhombic structure, with denser packing and, therefore, the most important for the barrier function, has its fraction significantly increased by the action of the composition according to the present invention on the skin, increasing the percentage of total crystallinity of the lipoprotein barrier, providing at the same time an improvement in hydration, elasticity, cutaneous relief, renewal and cellular energization (calcium gradient). Impact assay of the composition of the invention applied to biopsies of normal human skin The tests were carried out on fresh tissue samples (biopsies) of normal facial skin of women aged 60 (six millimeters) treated with the composition of the present invention versus placebo.

The study compared the impact of the treatment in the expression of proteins associated to the differentiation or structure and function of the derme-epidermis junction.

There was applied 20 μl, twice per day, of aqueous solution prepared with 5% of the composition of the invention pursuant to example 1 and water as placebo.

Involucrin, philagrin and integrin beta-1 were used as markers. The quantifications were carried out with the assistance of the software Image-Pro Analyzer, developed by Media Cybernetics, Inc.

Involucrin and philagrin, also known as proteins of the corneum envelope, were able to be used as efficient markers, because they participate in the process of forming the skin barrier.

Figure 8A:
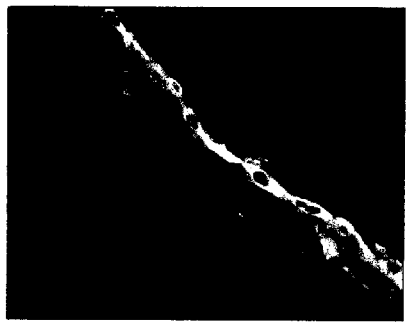
FIG. 8A shows results of immune colometric assay carried out with involucrin, where A and B correspond to placebo and composition of the present invention, respectively, at the moment of application of C and D correspond to placebo and composition of the present invention, respectively, after 48 hours.
Figure 8A:
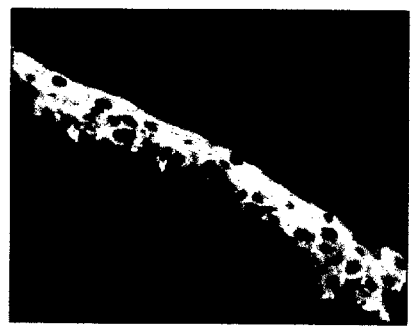
Figure 8A:
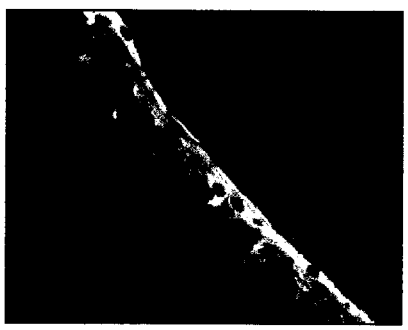
Figure 8A:
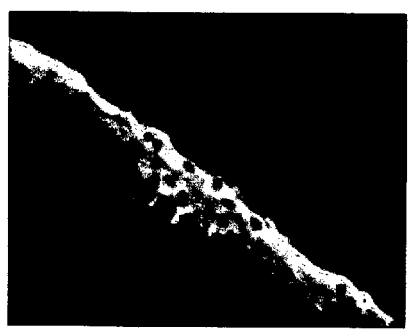

FIG. 8A shows the results of the tests of immune colometric assay carried out with involucrin, which acts in the differentiation process of corneocytes. In this test, A and D correspond to the examinations of the sample which received placebo initially and after 48 hours, respectively. B and C correspond to the examinations of the sample which received the composition of the invention initially and after 48 hours, respectively.

The qualitative analysis of the immune colometric assay shows a significant difference favorable to the sample treated with the composition of the present invention, especially after 48 hours.

Figure 8B:
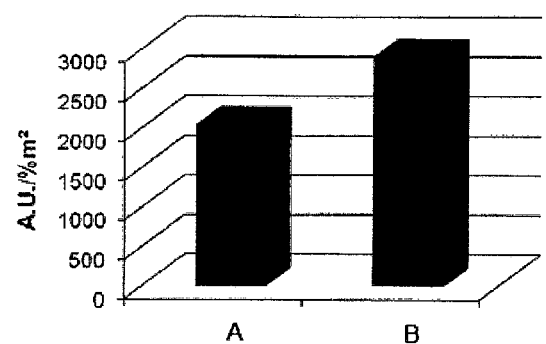
FIG. 8B shows a comparative quantification of results of immune colometric assay carried out with involucrin, where A and B correspond to placebo and composition of the present invention, respectively.

FIG. 8B shows a comparative quantification of this same test, revealing an increase of 42% in involucrin initially.

Figure 9A:
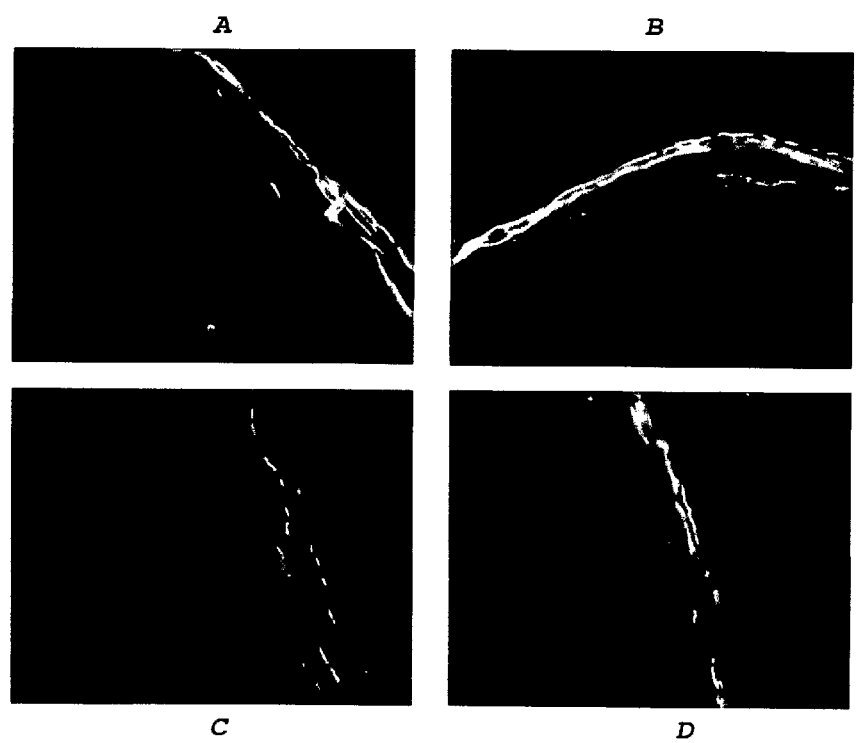
FIG. 9A shows results of immune colometric assay carried out with philagrin, where A and B correspond to placebo and composition of the present invention, respectively, at the moment of application of C and D correspond to placebo and composition of the present invention, respectively, after 48 hours.

FIG. 9A shows the results of the tests of immune colometric assay carried out with philagrin, which acts in the formation of lamellar gel and may indicate that the barrier thereafter acts independently, with long-lasting effect. In this assay, A and D correspond to the examinations of the sample which received placebo initially and after 48 hours, respectively. B and C correspond to the examinations of the sample which received the composition of the invention initially and after 48 hours, respectively.

The qualitative analysis of this assay of immune colometric assay shows a significant difference favorable to the sample treated with the composition of the present invention, especially initially.

Figure 9B:
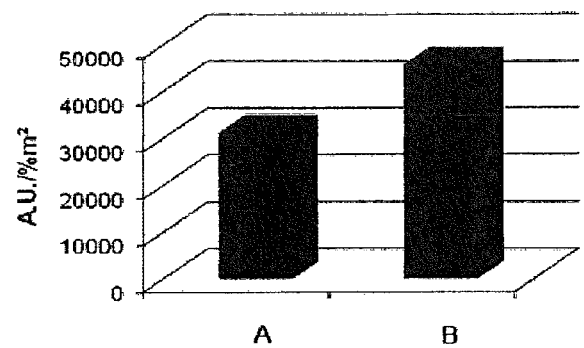
FIG. 9B shows comparative quantification of results of immune colometric assay carried out with philagrin, where A and B correspond to placebo and composition of the present invention, respectively.

FIG. 9B shows a comparative quantification of this same test, revealing an increase of 46% in philagrin initially.

Figure 10A:
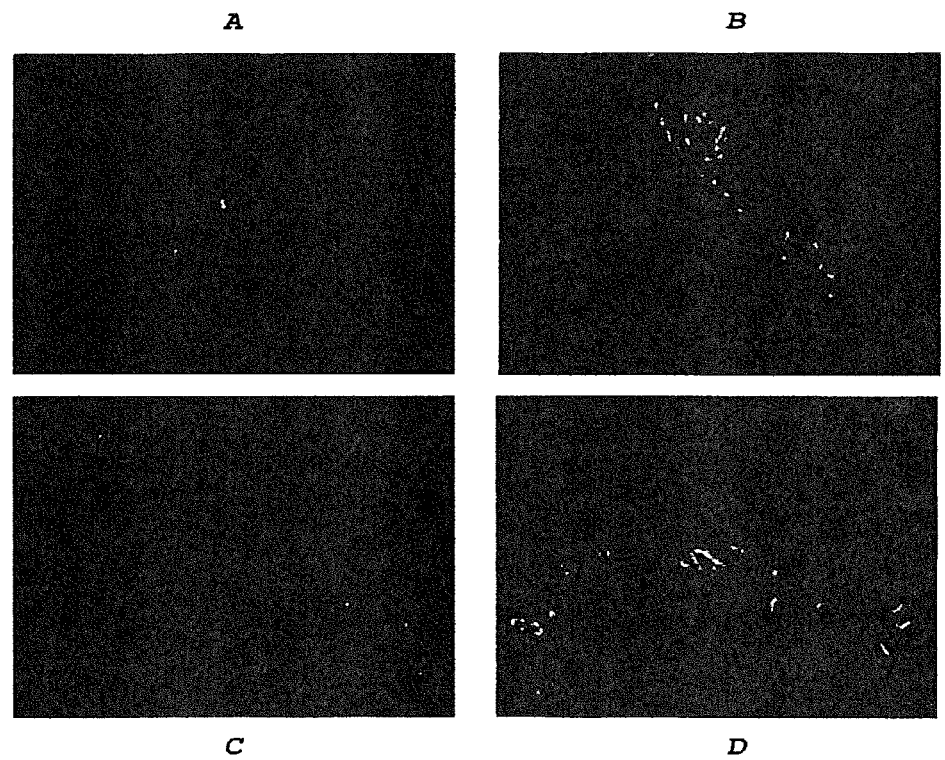
FIG. 10A shows results of immune colometric assay carried out with integrin beta-1, where A and B correspond to placebo and composition of the present invention, respectively, at the moment of application and C and D correspond to placebo and composition of the present invention, respectively, after 48 hours.

FIG. 10A shows the results of the tests of immune colometric assay carried out with integrin beta-1, which plays an important role in adhesion and cellular recognition, especially in the restoration of tissue, formation of keratinocytes. In this test, A and D correspond to the examinations of the sample which received placebo initially and after 48 hours, respectively. B and C correspond to the examinations of the sample which received the composition of the invention initially and after 48 hours, respectively.

The qualitative analysis of this immune colometric assay shows a significant difference favorable to the sample treated with the composition of the present invention.

Figure 10B:
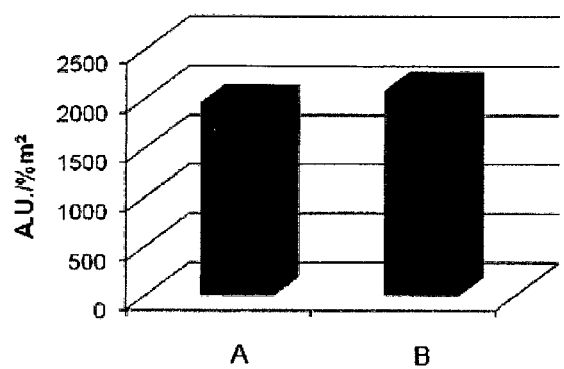
FIG. 10B shows comparative quantification of results of immune colometric assay carried out with integrin beta-1, where A and B correspond to placebo and composition of the present invention, respectively.
Figure 8A:
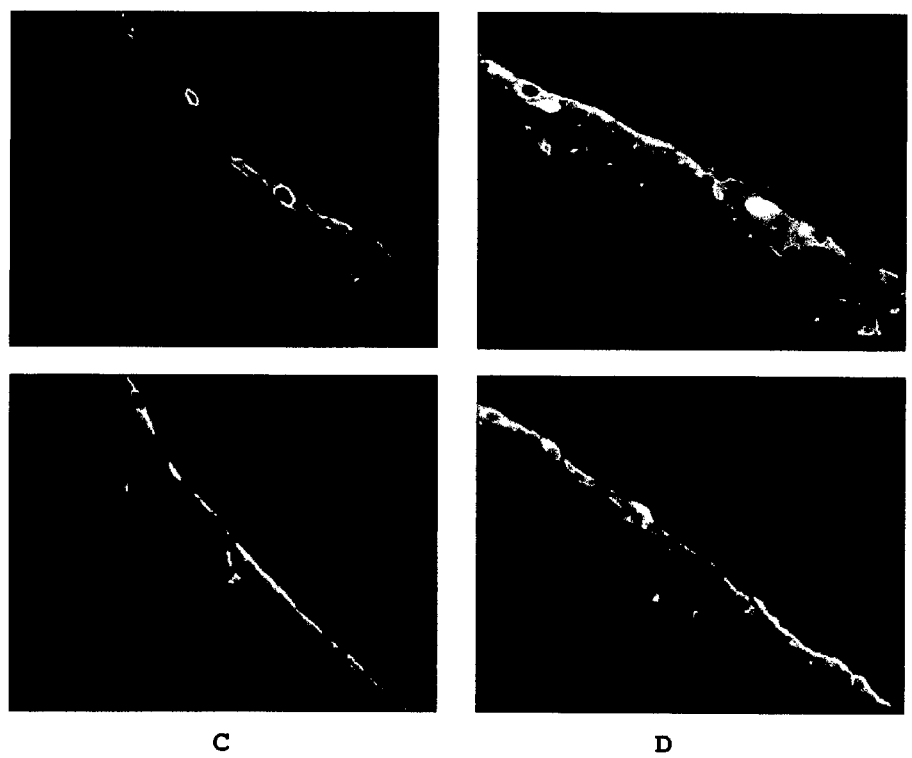
Figure 8B:
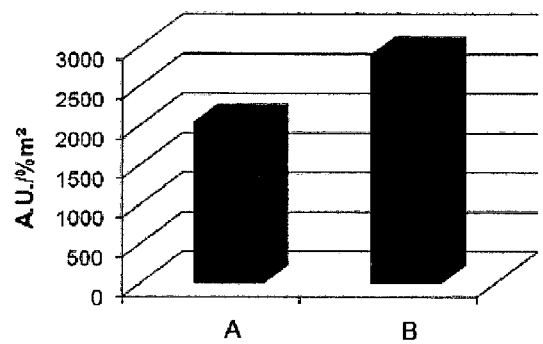
Figure 9A:
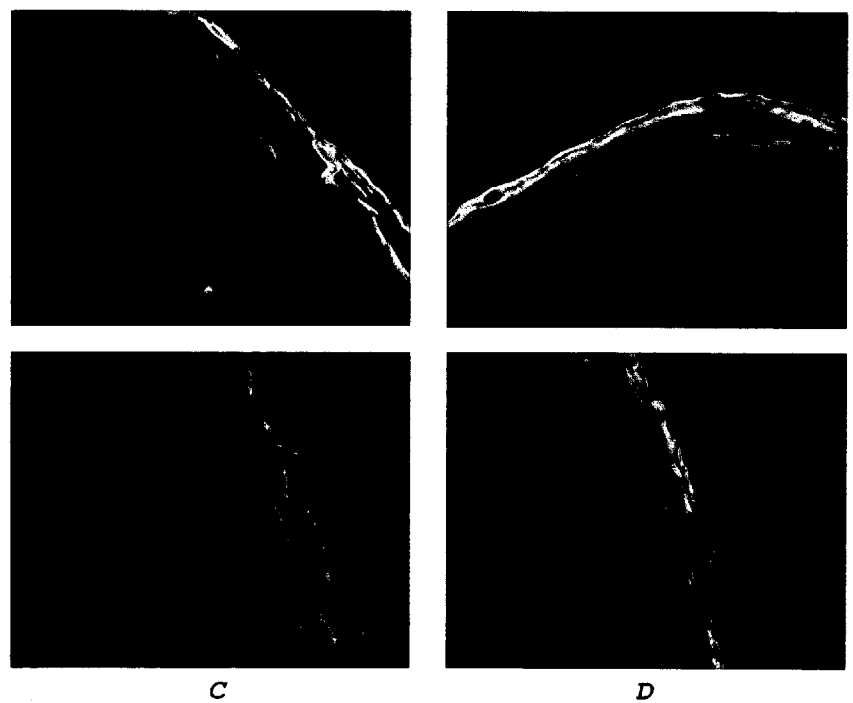
Figure 9B:
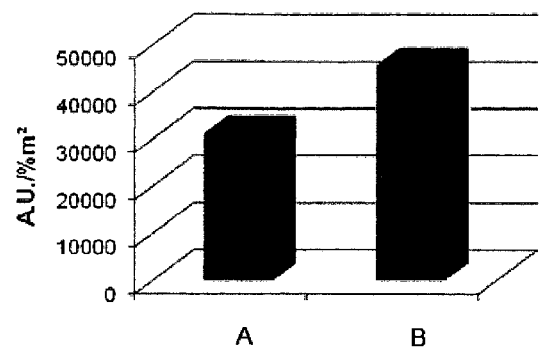
Figure 10A:
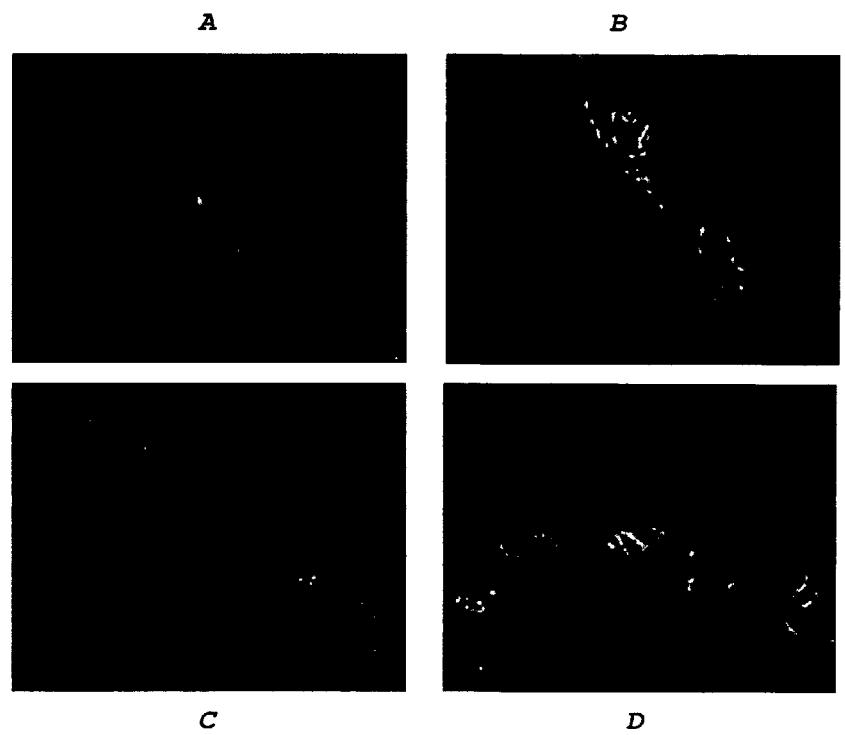
Figure 10B:
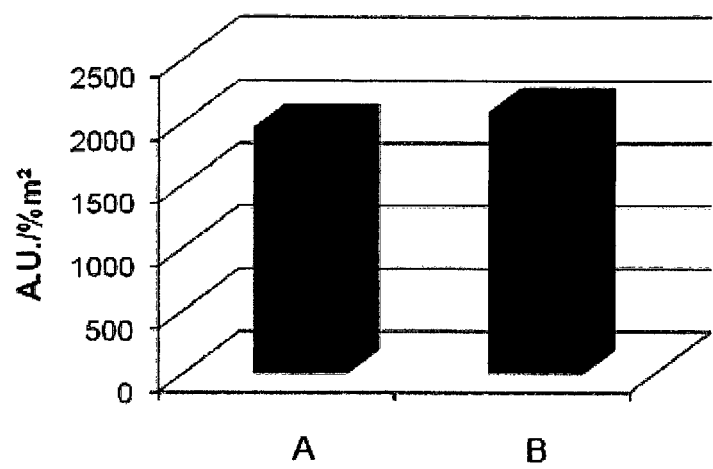

FIG. 10B shows a comparative quantification of this same test, demonstrating an increase of 7% of integrin beta-1 initially.

Additionally, after 48 hours, the expression of involucrin and philagrin in the biopsies treated with the composition of the invention shows a clear improvement compared to the skin treated with placebo. This improvement of the differentiation markers indicates a beneficial effect in terms of skin barrier, resulting in healthier skin.

In the same manner, an increase in the expression of integrin beta-1 is noted, assisting to improve the derme-epidermis communication.

The results of these tests demonstrate the effectiveness of the composition of the present invention for use as an active cosmetic ingredient.

It must be understood that the embodiments described above are merely illustrative and that other embodiments may occur to persons skilled in the art, having substantially equivalent functions and results. Consequently, the present invention should not be considered limited to the embodiments described herein.

By way of the teachings set forth in the text and in the examples, persons skilled in the art will immediately appreciate the advantages of the invention and propose variations and equivalent alternatives of embodiment, without straying from the scope of the invention, as defined in the accompanying claims.

The invention claimed is:

1. An oil-in-glycol cosmetic composition comprising sucrose stearate, behenyl alcohol, at least one glycol butylene, sucrose tristearate, and arginine; wherein the composition restores the cutaneous barrier.

2. The composition according to claim 1, wherein the composition comprises 10% to 20% by weight of the sucrose stearate in relation to the total weight of the composition.

3. The composition according to claim 1, wherein the composition comprises 10% to 20% by weight of the behenyl alcohol in relation to the total weight of the composition.

4. The composition according to claim 1, wherein the composition comprises 40% to 65% by weight of the glycol butylenes in relation to the total weight of the composition.

5. The composition according to claim 1, wherein the composition comprises 5% to 30% by weight of the arginine in relation to the total weight of the composition.

6. The composition according to claim 1, wherein the composition comprises about 2% of the arginine by weight in relation to the total weight of the composition.

7. The composition according to claim 1, wherein the arginine is esterified arginine.

8. The composition according to claim 1, wherein the weight, ratio of sucrose stearate to sucrose tristearate is about 2:1.

9. A cosmetic product comprising 1 to 30% by weight of the cosmetic composition according to claim 1.

* * * * *